Figure 4:
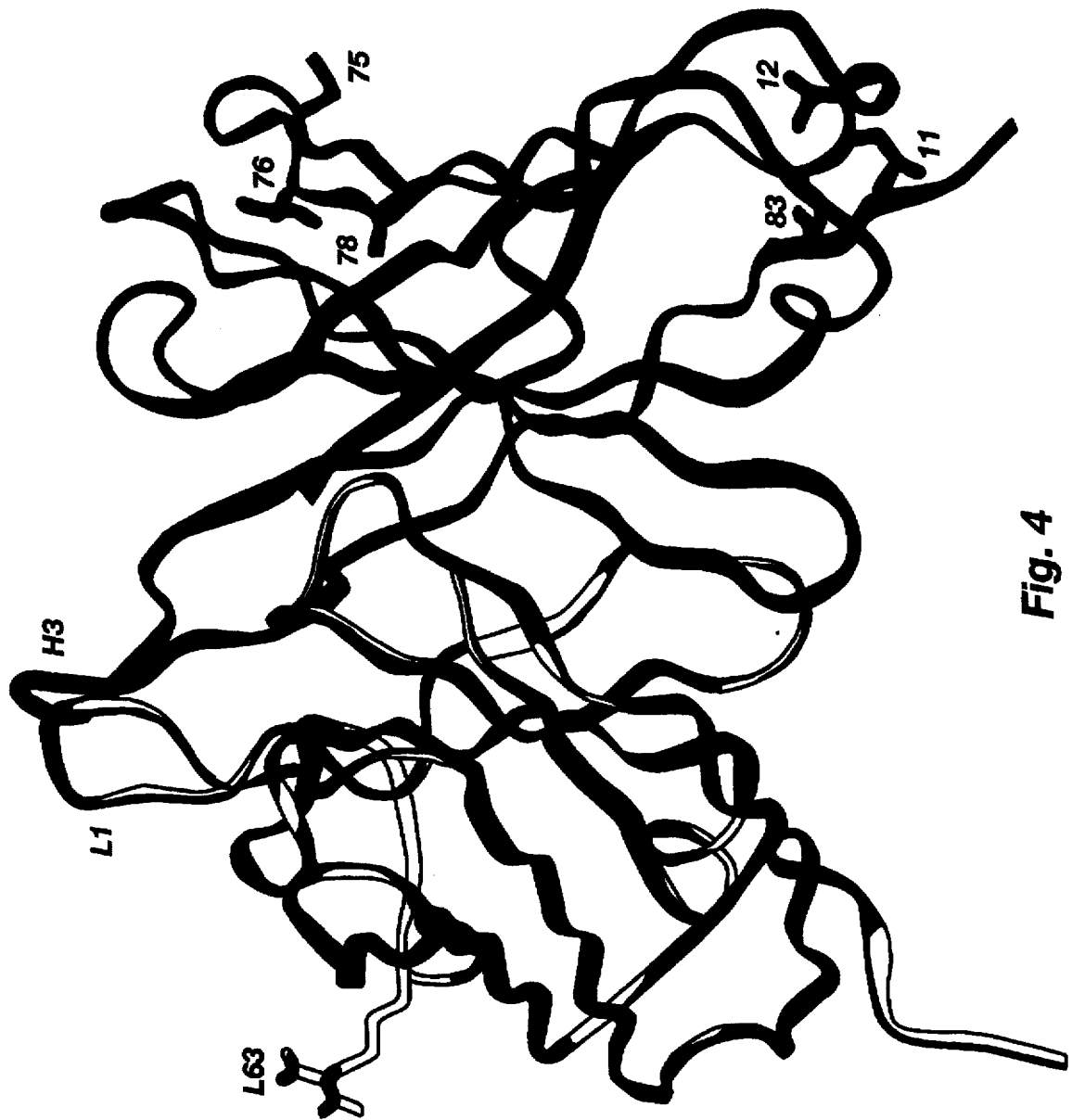

United States Patent [19]

Rodriguez et al.

[11] Patent Number: 5,712,120
[45] Date of Patent: Jan. 27, 1998

[54] METHOD FOR OBTAINING MODIFIED IMMUNOGLOBULINS WITH REDUCED IMMUNOGENICITY OF MURINE ANTIBODY VARIABLE DOMAINS, COMPOSITIONS CONTAINING THEM

[75] Inventors: Rolando Perez Rodriguez, Vibora; Christina Maria Mateo de Acosta del Rio, Vedado; Josefa Lombardero Valladares, Vibora, all of Cuba

[73] Assignee: Centro De Immunologia Molecular, Havana, Cuba

[21] Appl. No.: 497,312

[22] Filed: Jun. 30, 1995

[30] Foreign Application Priority Data

Jun. 30, 1994 [CU] Cuba ............................................ 80/94

[51] Int. Cl.$^6$ ............................ C12N 15/13; C07K 16/00; C07H 21/04; A61K 39/395
[52] U.S. Cl. .................... 435/69.6; 435/70.21; 435/71.1; 435/328; 435/69.7; 530/387.3; 536/23.53; 424/133.1; 424/135.8
[58] Field of Search .............................. 435/69.6, 172.3, 435/70.21, 71.1, 328, 69.7; 424/133.1, 135.1; 530/387.3; 536/23.53

[56] References Cited

FOREIGN PATENT DOCUMENTS 0 519 596 A1  12/1992  European Pat. Off. .

OTHER PUBLICATIONS

Article entitled: A Possible Procedure for Reducing the Immunogenicity of Antibody Variable Domains While Preserving Their Ligand–Binding Properties. Author: Eduardo A. Padlan Published in Molecular Immunology, vol. 28, No. 4/5, pp. 489–498, 1991.

Reyes, VE et al. Methods in Enzymology 202:225–238 (1991).

Margalit, H. et al. Journal of Immunology 138(7):2213–2229 (1987).

Foote J. et al Journal of Molecular Biology 224:487–499 (1992).

Chothia C. et al. Journal of Molecular Biology 196:901–917 (1987).

*Primary Examiner*—Toni R. Scheiner
*Assistant Examiner*—John Lucas
*Attorney, Agent, or Firm*—Trask, Britt & Rossa

[57] ABSTRACT

Modified chimaeric antibodies, and antibody heavy and light chains, which comprise variable domains derived from a first mammalian species, usually mouse, and constant domains from a second mammalian species, usually human. Modification concerns the variable domains, in particular the framework regions of the variable domains. The modifications are made only in T-cell antigenic structures present in framework regions, and do not cover canonical structures or Vernier zone. The modifications adapt the amino acid sequences concerned to those occurring in corresponding antibodies derived from said second mammalian species. Thus, the modified chimaeric antibodies retain the original antigen recognition and binding properties but become less immunogenic to said second mammalian species, which improves their therapeutical utility with said second mammalian species. Recombinant DNA technology may be used to construct and produce the modified chimaeric antibodies.

4 Claims, 10 Drawing Sheets

FIGURE 1: DEDUCED AMINO ACID SEQUENCES

A    VK OF MURINE R3 ANTIBODY

D V L M T Q I P L S L P V S L G D Q A S I S C R S S Q
N I N I V H S N G N T Y L D W Y L Q K P G Q S P N L L
I Y K V S N R F S G V P D R F R G S G S G T D F T L K
I S R V E A E D L G V Y Y C F Q Y S H V P W T F G G G
T K L E I K R A

B    VH OF MURINE R3 ANTIBODY

Q V Q L Q Q P G A E L V K P G A S V K L S C K A S G Y
T F T N Y Y I Y W V K Q R P G Q G L E W I G G I N P T
S G G S N F N E K F K T K A T L T V D E S S T T A Y M
Q L S S L T S E D S A V Y Y C T R Q G L W F D S D G R
G F D F W G Q G T T L T V S S

FIGURE 2: VARIABLE REGION OF THE HEAVY CHAIN OF IOR-R3

|   | 1 | 2 | 3 | 4 | 5 | 6 | 7 | 8 | 9 | 10 | 11 | 12 |
|---|---|---|---|---|---|---|---|---|---|---|---|---|
| A | GLN | VAL | GLN | LEU | GLN | GLN | PRO | GLY | ALA | GLU | LEU | VAL |
| B | GLN | VAL | GLN | LEU | VAL | GLN | SER | GLY | ALA | GLU | VAL | LYS |
| C | GLN | VAL | GLN | LEU | GLN | GLN | PRO | GLY | ALA | GLU | VAL | LYS |

|   | 13 | 14 | 15 | 16 | 17 | 18 | 19 | 20 | 21 | 22 | 23 | 24 |
|---|---|---|---|---|---|---|---|---|---|---|---|---|
| A | LYS | PRO | GLY | ALA | SER | VAL | LYS | LEU | SER | CYS | LYS | ALA |
| B | LYS | PRO | GLY | ALA | SER | VAL | LYS | VAL | SER | CYS | LYS | ALA |
| C | LYS | PRO | GLY | ALA | SER | VAL | LYS | LEU | SER | CYS | LYS | ALA |

|   | 25 | 26 | 27 | 28 | 29 | 30 | 31 | 32 | 33 | 34 | 35 | 36 |
|---|---|---|---|---|---|---|---|---|---|---|---|---|
| A | SER | GLY | TYR | THR | PHE | THR | ASN | TYR | TYR | ILE | TYR | TRP |
| B | SER | GLY | TYR | THR | PHE | ASN |  |  |  |  |  | TRP |
| C | SER | GLY | TYR | THR | PHE | THR | ASN | TYR | TYR | ILE | TYR | TRP |

|   | 37 | 38 | 39 | 40 | 41 | 42 | 43 | 44 | 45 | 46 | 47 | 48 |
|---|---|---|---|---|---|---|---|---|---|---|---|---|
| A | VAL | LYS | GLN | ARG | PRO | GLY | GLN | GLY | LEU | GLU | TRP | ILE |
| B | VAL | ARG | GLN | ALA | PRO | GLY | GLN | GLY | LEU | GLU | TRP | MET |
| C | VAL | LYS | GLN | ARG | PRO | GLY | GLN | GLY | LEU | GLU | TRP | ILE |

|   | 49 | 50 | 51 | 52 | 52A | 53 | 54 | 55 | 56 | 57 | 58 | 59 |
|---|---|---|---|---|---|---|---|---|---|---|---|---|
| A | GLY | GLY | ILE | ASN | PRO | THR | SER | GLY | GLY | SER | ASN | PHE |
| B | GLY |  |  |  |  |  |  |  |  |  |  |  |
| C | GLY | GLY | ILE | ASN | PRO | THR | SER | GLY | GLY | SER | ASN | PHE |

|   | 60 | 61 | 62 | 63 | 64 | 65 | 66 | 67 | 68 | 69 | 70 | 71 |
|---|---|---|---|---|---|---|---|---|---|---|---|---|
| A | ASN | GLU | LYS | PHE | LYS | THR | LYS | ALA | THR | LEU | THR | VAL |
| B |  |  |  |  |  |  | ARG | VAL | THR | MET | THR | ARG |
| C | ASN | GLU | LYS | PHE | LYS | THR | LYS | ALA | THR | LEU | THR | VAL |

|   | 72 | 73 | 74 | 75 | 76 | 77 | 78 | 79 | 80 | 81 | 82 | 82A |
|---|---|---|---|---|---|---|---|---|---|---|---|---|
| A | ASP | GLU | SER | SER | THR | THR | ALA | TYR | MET | GLN | LEU | SER |
| B | ASP | THR | SER | THR | SER | THR | VAL | TYR | MET | GLU | LEU | SER |
| C | ASP | GLU | SER | THR | SER | THR | VAL | TYR | MET | GLN | LEU | SER |

|   | 82B | 82C | 83 | 84 | 85 | 86 | 87 | 88 | 89 | 90 | 91 | 92 |
|---|---|---|---|---|---|---|---|---|---|---|---|---|
| A | SER | LEU | THR | SER | GLU | ASP | SER | ALA | VAL | TYR | TYR | CYS |
| B | SER | LEU | ARG | SER | GLU | ASP | THR | ALA | VAL | TYR | TYR | CYS |
| C | SER | LEU | ARG | SER | GLU | ASP | SER | ALA | VAL | TYR | TYR | CYS |

|   | 93 | 94 | 95 | 96 | 97 | 98 | 99 | 100 | 100A | 100B | 100C | 100D |
|---|---|---|---|---|---|---|---|---|---|---|---|---|
| A | THR | ARG | GLN | GLY | LEU | TRP | PHE | ASP | SER | ASP | GLY | ARG |
| B | ALA | ARG |  |  |  |  |  |  |  |  |  |  |
| C | THR | ARG | GLN | GLY | LEU | TRP | PHE | ASP | SER | ASP | GLY | ARG |

|   | 100E | 100F | 101 | 102 | 103 | 104 | 105 | 106 | 107 | 108 | 109 | 110 |
|---|---|---|---|---|---|---|---|---|---|---|---|---|
| A | GLY | PHE | ASP | PHE | TRP | GLY | GLN | GLY | THR | THR | LEU | THR |
| B |  |  |  |  | TRP | GLY | GLN | GLY | THR | LEU | VAL | THR |
| C | GLY | PHE | ASP | PHE | TRP | GLY | GLN | GLY | THR | THR | LEU | THR |

|   | 111 | 112 | 113 |
|---|---|---|---|
| A | VAL | SER | SER |
| B | VAL | SER | SER |
| C | VAL | SER | SER |

FIGURE 3: VARIABLE REGION OF THE LIGHT CHAIN OF IOR-R3.

|   | 1   | 2   | 3   | 4   | 5   | 6   | 7   | 8   | 9   | 10  | 11  | 12  |
|---|-----|-----|-----|-----|-----|-----|-----|-----|-----|-----|-----|-----|
| A | ASP | VAL | LEU | MET | THR | GLN | ILE | PRO | LEU | SER | LEU | PRO |
| B | ASP | VAL | VAL | MET | THR | GLN | SER | PRO | LEU | SER | LEU | PRO |
| C | ASP | VAL | LEU | MET | THR | GLN | ILE | PRO | LEU | SER | LEU | PRO |

|   | 13  | 14  | 15  | 16  | 17  | 18  | 19  | 20  | 21  | 22  | 23  | 24  |
|---|-----|-----|-----|-----|-----|-----|-----|-----|-----|-----|-----|-----|
| A | VAL | SER | LEU | GLY | ASP | GLN | ALA | SER | ILE | SER | CYS | ARG |
| B | VAL | THR | LEU | GLY | GLN | PRO | ALA | SER | ILE | SER | CYS |     |
| C | VAL | SER | LEU | GLY | ASP | GLN | ALA | SER | ILE | SER | CYS | ARG |

|   | 25  | 26  | 27  | 27A | 27B | 27C | 27D | 27E | 28  | 29  | 30  | 31  |
|---|-----|-----|-----|-----|-----|-----|-----|-----|-----|-----|-----|-----|
| A | SER | SER | GLN | ASN | ILE | VAL | HIS | SER | ASN | GLY | ASN | THR |
| B |     |     |     |     |     |     |     |     |     |     |     |     |
| C | SER | SER | GLN | ASN | ILE | VAL | HIS | SER | ASN | GLY | ASN | THR |

|   | 32  | 33  | 34  | 35  | 36  | 37  | 38  | 39  | 40  | 41  | 42  | 43  |
|---|-----|-----|-----|-----|-----|-----|-----|-----|-----|-----|-----|-----|
| A | TYR | LEU | ASP | TRP | TYR | LEU | GLN | LYS | PRO | GLY | GLN | SER |
| B |     |     |     | TRP | PHE | GLN | GLN | ARG | PRO | GLY | GLN | SER |
| C | TYR | LEU | ASP | TRP | TYR | LEU | GLN | LYS | PRO | GLY | GLN | SER |

|   | 44  | 45  | 46  | 47  | 48  | 49  | 50  | 51  | 52  | 53  | 54  | 55  |
|---|-----|-----|-----|-----|-----|-----|-----|-----|-----|-----|-----|-----|
| A | PRO | ASN | LEU | LEU | ILE | TYR | LYS | VAL | SER | ASN | ARG | PHE |
| B | PRO | ARG | ARG | LEU | ILE | TYR |     |     |     |     |     |     |
| C | PRO | ASN | LEU | LEU | ILE | TYR | LYS | VAL | SER | ASN | ARG | PHE |

|   | 56  | 57  | 58  | 59  | 60  | 61  | 62  | 63  | 64  | 65  | 66  | 67  |
|---|-----|-----|-----|-----|-----|-----|-----|-----|-----|-----|-----|-----|
| A | SER | GLY | VAL | PRO | ASP | ARG | PHE | ARG | GLY | SER | GLY | SER |
| B |     | GLY | VAL | PRO | ASP | ARG | PHE | SER | GLY | SER | GLY | SER |
| C | SER | GLY | VAL | PRO | ASP | ARG | PHE | ARG | GLY | SER | GLY | SER |

|   | 68  | 69  | 70  | 71  | 72  | 73  | 74  | 75  | 76  | 77  | 78  | 79  |
|---|-----|-----|-----|-----|-----|-----|-----|-----|-----|-----|-----|-----|
| A | GLY | THR | ASP | PHE | THR | LEU | LYS | ILE | SER | ARG | VAL | GLU |
| B | GLY | THR | ASP | PHE | THR | LEU | LYS | ILE | SER | ARG | VAL | GLU |
| C | GLY | THR | ASP | PHE | THR | LEU | LYS | ILE | SER | ARG | VAL | GLU |

|   | 80  | 81  | 82  | 83  | 84  | 85  | 86  | 87  | 88  | 89  | 90  | 91  |
|---|-----|-----|-----|-----|-----|-----|-----|-----|-----|-----|-----|-----|
| A | ALA | GLU | ASP | LEU | GLY | VAL | TYR | TYR | CYS | PHE | GLN | TYR |
| B | ALA | GLU | ASP | VAL | GLY | VAL | TYR | TYR | CYS |     |     |     |
| C | ALA | GLU | ASP | LEU | GLY | VAL | TYR | TYR | CYS | PHE | GLN | TYR |

|   | 92  | 93  | 94  | 95  | 96  | 97  | 98  | 99  | 100 | 101 | 102 | 103 |
|---|-----|-----|-----|-----|-----|-----|-----|-----|-----|-----|-----|-----|
| A | SER | HIS | VAL | PRO | TRP | THR | PHE | GLY | GLY | GLY | THR | LYS |
| B |     |     |     |     |     |     | PHE | GLY | GLN | GLY | THR | LYS |
| C | SER | HIS | VAL | PRO | TRP | THR | PHE | GLY | GLY | GLY | THR | LYS |

|   | 104 | 105 | 106 | 107 | 108 |
|---|-----|-----|-----|-----|-----|
| A | LEU | GLU | ILE | LYS | ARG |
| B | VAL | GLU | ILE | LYS | ARG |
| C | LEU | GLU | ILE | LYS | ARG |

FIGURE 7: VARIABLE REGION OF THE HEAVY CHAIN OF IOR-T 1.

|   | 1 | 2 | 3 | 4 | 5 | 6 | 7 | 8 | 9 | 10 | 11 | 12 |
|---|---|---|---|---|---|---|---|---|---|----|----|----|
| A | GLU | VAL | LYS | LEU | VAL | GLN | SER | GLY | GLY | GLY | LEU | VAL |
| B | GLU | VAL | GLN | LEU | LEU | GLU | SER | GLY | GLY | GLY | LEU | VAL |
| C | GLU | VAL | GLN | LEU | LEU | GLU | SER | GLY | GLY | GLY | LEU | VAL |

|   | 13 | 14 | 15 | 16 | 17 | 18 | 19 | 20 | 21 | 22 | 23 | 24 |
|---|----|----|----|----|----|----|----|----|----|----|----|----|
| A | LYS | PRO | GLY | GLY | SER | LEU | LYS | LEU | SER | CYS | ALA | ALA |
| B | GLN | PRO | GLY | GLY | SER | LEU | ARG | LEU | SER | CYS | ALA | ALA |
| C | GLN | PRO | GLY | GLY | SER | LEU | ARG | LEU | SER | CYS | ALA | ALA |

|   | 25 | 26 | 27 | 28 | 29 | 30 | 31 | 32 | 33 | 34 | 35 | 36 |
|---|----|----|----|----|----|----|----|----|----|----|----|----|
| A | SER | GLY | PHE | LYS | PHE | SER | ARG | TYR | ALA | MET | SER | TRP |
| B | SER | GLY | PHE | THR | PHE | SER |    |    |    |    |    | TRP |
| C | SER | GLY | PHE | LYS | PHE | SER | ARG | TYR | ALA | MET | SER | TRP |

|   | 37 | 38 | 39 | 40 | 41 | 42 | 43 | 44 | 45 | 46 | 47 | 48 |
|---|----|----|----|----|----|----|----|----|----|----|----|----|
| A | VAL | ARG | GLN | THR | PRO | GLU | LYS | ARG | LEU | GLU | TRP | VAL |
| B | VAL | ARG | GLN | ALA | PRO | GLY | LYS | GLY | LEU | GLU | TRP | VAL |
| C | VAL | ARG | GLN | ALA | PRO | GLY | LYS | ARG | LEU | GLU | TRP | VAL |

|   | 49 | 50 | 51 | 52 | 52A | 53 | 54 | 55 | 56 | 57 | 58 | 59 |
|---|----|----|----|----|-----|----|----|----|----|----|----|----|
| A | ALA | THR | ILE | SER | SER | GLY | GLY | SER | SER | HIS | LEU | LEU |
| B | SER |    |    |    |     |    |    |    |    |    |    |    |
| C | SER | THR | ILE | SER | SER | GLY | GLY | SER | SER | HIS | LEU | LEU |

|   | 60 | 61 | 62 | 63 | 64 | 65 | 66 | 67 | 68 | 69 | 70 | 71 |
|---|----|----|----|----|----|----|----|----|----|----|----|----|
| A | SER | ARG | GLN | CYS | GLU | GLY | ARG | PHE | THR | ILE | SER | ARG |
| B |    |    |    |    |    |    | ARG | PHE | THR | ILE | SER | ARG |
| C | SER | ARG | GLN | CYS | GLU | GLY | ARG | PHE | THR | ILE | SER | ARG |

|   | 72 | 73 | 74 | 75 | 76 | 77 | 78 | 79 | 80 | 81 | 82 | 82A |
|---|----|----|----|----|----|----|----|----|----|----|----|-----|
| A | ASP | ASN | VAL | LYS | ASN | THR | LEU | TYR | LEU | GLN | MET | SER |
| B | ASP | ASN | SER | LYS | ASN | THR | LEU | TYR | LEU | GLN | MET | ASN |
| C | ASP | ASN | VAL | LYS | ASN | THR | LEU | TYR | LEU | GLN | MET | SER |

|   | 82B | 82C | 83 | 84 | 85 | 86 | 87 | 88 | 89 | 90 | 91 | 92 |
|---|-----|-----|----|----|----|----|----|----|----|----|----|----|
| A | SER | LEU | ARG | SER | GLU | ASP | THR | ALA | MET | TYR | TYR | CYS |
| B | SER | LEU | ARG | ALA | GLU | ASP | THR | ALA | VAL | TYR | TYR | CYS |
| C | SER | LEU | ARG | SER | GLU | ASP | THR | ALA | MET | TYR | TYR | CYS |

|   | 93 | 94 | 95 | 96 | 97 | 98 | 99 | 100 | 100A | 100B | 101 | 102 |
|---|----|----|----|----|----|----|----|-----|------|------|-----|-----|
| A | ALA | ARG | ARG | ASP | TYR | ASP | LEU | ASP | TYR | PHE | ALA | SER |
| B | ALA | LYS |    |    |    |    |    |     |      |      |     |     |
| C | ALA | ARG | ARG | ASP | TYR | ASP | LEU | ASP | TYR | PHE | ALA | SER |

|   | 103 | 104 | 105 | 106 | 107 | 108 | 109 | 110 | 111 | 112 | 113 |
|---|-----|-----|-----|-----|-----|-----|-----|-----|-----|-----|-----|
| A | TRP | GLY | GLN | GLY | THR | THR | LEU | THR | VAL | SER | SER |
| B | TRP | GLY | GLN | GLY | THR | LEU | VAL | THR | VAL | SER | SER |
| C | TRP | GLY | GLN | GLY | THR | LEU | VAL | THR | VAL | SER | SER |

FIGURE 8: VARIABLE REGION OF THE LIGHT CHAIN OF IOR-T 1.

|   | 1 | 2 | 3 | 4 | 5 | 6 | 7 | 8 | 9 | 10 | 11 | 12 |
|---|---|---|---|---|---|---|---|---|---|----|----|----|
| A | ASP | ILE | VAL | MET | THR | GLN | ASP | GLN | LYS | PHE | MET | SER |
| B | GLU | ILE | VAL | MET | THR | GLN | SER | PRO | ALA | THR | LEU | SER |
| C | ASP | ILE | VAL | MET | THR | GLN | ASP | GLN | LYS | PHE | MET | SER |

|   | 13 | 14 | 15 | 16 | 17 | 18 | 19 | 20 | 21 | 22 | 23 | 24 |
|---|----|----|----|----|----|----|----|----|----|----|----|----|
| A | THR | SER | VAL | GLY | ASP | ARG | VAL | SER | VAL | THR | CYS | LYS |
| B | VAL | SER | PRO | GLY | GLU | ARG | ALA | THR | LEU | SER | CYS |  |
| C | THR | SER | VAL | GLY | ASP | ARG | VAL | SER | VAL | THR | CYS | LYS |

|   | 25 | 26 | 27 | 28 | 29 | 30 | 31 | 32 | 33 | 34 | 35 | 36 |
|---|----|----|----|----|----|----|----|----|----|----|----|----|
| A | ALA | SER | GLN | ASN | ALA | GLY | THR | ASN | VAL | ALA | TRP | TYR |
| B |  |  |  |  |  |  |  |  |  |  | TRP | TYR |
| C | ALA | SER | GLN | ASN | ALA | GLY | THR | ASN | VAL | ALA | TRP | TYR |

|   | 37 | 38 | 39 | 40 | 41 | 42 | 43 | 44 | 45 | 46 | 47 | 48 |
|---|----|----|----|----|----|----|----|----|----|----|----|----|
| A | GLN | GLN | LYS | PRO | GLY | GLN | SER | PRO | LYS | ALA | LEU | ILE |
| B | GLN | GLN | LYS | PRO | GLY | GLN | PRO | PRO | ARG | LEU | LEU | ILE |
| C | GLN | GLN | LYS | PRO | GLY | GLN | SER | PRO | LYS | ALA | LEU | ILE |

|   | 49 | 50 | 51 | 52 | 53 | 54 | 55 | 56 | 57 | 58 | 59 | 60 |
|---|----|----|----|----|----|----|----|----|----|----|----|----|
| A | TYR | SER | ALA | SER | SER | ARG | ASN | SER | GLY | VAL | PRO | ASP |
| B | TYR |  |  |  |  |  |  |  | GLY | ILE | PRO | ALA |
| C | TYR | SER | ALA | SER | SER | ARG | ASN | SER | GLY | VAL | PRO | ALA |

|   | 61 | 62 | 63 | 64 | 65 | 66 | 67 | 68 | 69 | 70 | 71 | 72 |
|---|----|----|----|----|----|----|----|----|----|----|----|----|
| A | ARG | PHE | THR | GLY | SER | GLY | SER | GLY | THR | ASP | PHE | THR |
| B | ARG | PHE | SER | GLY | SER | GLY | SER | GLY | THR | GLU | PHE | THR |
| C | ARG | PHE | SER | GLY | SER | GLY | SER | GLY | THR | ASP | PHE | THR |

|   | 73 | 74 | 75 | 76 | 77 | 78 | 79 | 80 | 81 | 82 | 83 | 84 |
|---|----|----|----|----|----|----|----|----|----|----|----|----|
| A | LEU | THR | ILE | SER | ASN | VAL | GLN | SER | GLU | ASP | LEU | ALA |
| B | LEU | THR | ILE | SER | ARG | LEU | GLN | SER | GLU | ASP | PHE | ALA |
| C | LEU | THR | ILE | SER | ASN | VAL | GLN | SER | GLU | ASP | PHE | ALA |

|   | 85 | 86 | 87 | 88 | 89 | 90 | 91 | 92 | 93 | 94 | 95 | 95A |
|---|----|----|----|----|----|----|----|----|----|----|----|-----|
| A | GLU | TYR | PHE | CYS | GLN | GLN | TYR | ASN | SER | TYR | PRO | LEU |
| B | VAL | TYR | TYR | CYS |  |  |  |  |  |  |  |  |
| C | VAL | TYR | TYR | CYS | GLN | GLN | TYR | ASN | SER | TYR | PRO | LEU |

|   | 96 | 97 | 98 | 99 | 100 | 101 | 102 | 103 | 104 | 105 | 106 | 107 |
|---|----|----|----|----|-----|-----|-----|-----|-----|-----|-----|-----|
| A | VAL | THR | PHE | GLY | ALA | GLY | THR | LYS | LEU | GLU | LEU | LYS |
| B |  |  | PHE | GLY | GLN | GLY | THR | ARG | VAL | GLU | ILE | LYS |
| C | VAL | THR | PHE | GLY | ALA | GLY | THR | LYS | LEU | GLU | LEU | LYS |

|   | 108 | 109 |
|---|-----|-----|
| A | ARG | ALA |
| B | ARG | GLU |
| C | ARG | ALA |

FIGURE 9: VARIABLE REGION OF THE HEAVY CHAIN OF IOR-CEA-1.

| | 1 | 2 | 3 | 4 | 5 | 6 | 7 | 8 | 9 | 10 | 11 | 12 |
|---|---|---|---|---|---|---|---|---|---|---|---|---|
| A | GLN | PRO | LYS | LEU | LEU | GLU | SER | GLY | GLY | ASP | LEU | VAL |
| B | GLN | VAL | GLN | LEU | VAL | GLN | SER | GLY | ALA | GLU | VAL | LYS |
| C | GLN | VAL | GLN | LEU | VAL | GLN | SER | GLY | ALA | GLU | LEU | VAL |

| | 13 | 14 | 15 | 16 | 17 | 18 | 19 | 20 | 21 | 22 | 23 | 24 |
|---|---|---|---|---|---|---|---|---|---|---|---|---|
| A | LYS | PRO | GLU | ALA | SER | LEU | ASN | CYS | SER | CYS | ALA | VAL |
| B | LYS | PRO | GLY | ALA | SER | LEU | LYS | VAL | SER | CYS | LYS | ALA |
| C | LYS | PRO | GLY | ALA | SER | LEU | ASN | CYS | SER | CYS | ALA | VAL |

| | 25 | 26 | 27 | 28 | 29 | 30 | 31 | 32 | 33 | 34 | 35 | 36 |
|---|---|---|---|---|---|---|---|---|---|---|---|---|
| A | SER | GLY | PHE | PRO | PHE | ASN | ARG | TYR | ALA | MET | SER | TRP |
| B | SER | GLY | TYR | THR | PHE | THR | | | | | | TRP |
| C | SER | GLY | PHE | PRO | PHE | ASN | ARG | TYR | ALA | MET | SER | TRP |

| | 37 | 38 | 39 | 40 | 41 | 42 | 43 | 44 | 45 | 46 | 47 | 48 |
|---|---|---|---|---|---|---|---|---|---|---|---|---|
| A | VAL | LEU | GLN | THR | PRO | GLU | LYS | ARG | LEU | GLU | TRP | VAL |
| B | VAL | ARG | GLN | ALA | PRO | GLY | GLN | ARG | LEU | GLU | TRP | MET |
| C | VAL | LEU | GLN | THR | PRO | GLU | LYS | ARG | LEU | GLU | TRP | VAL |

| | 49 | 50 | 51 | 52 | 52A | 53 | 54 | 55 | 56 | 57 | 58 | 59 |
|---|---|---|---|---|---|---|---|---|---|---|---|---|
| A | ALA | PHE | ILE | SER | SER | ASP | ASP | GLY | ILE | ALA | TYR | TYR |
| B | GLY | | | | | | | | | | | |
| C | ALA | PHE | ILE | SER | SER | ASP | ASP | GLY | ILE | ALA | TYR | TYR |

| | 60 | 61 | 62 | 63 | 64 | 65 | 66 | 67 | 68 | 69 | 70 | 71 |
|---|---|---|---|---|---|---|---|---|---|---|---|---|
| A | ALA | GLU | SER | LYS | GLY | TYR | ARG | PHE | THR | ILE | SER | ARG |
| B | | | | | | | ARG | VAL | THR | ILE | THR | ARG |
| C | ALA | GLU | SER | LYS | GLY | TYR | ARG | PHE | THR | ILE | SER | ARG |

| | 72 | 73 | 74 | 75 | 76 | 77 | 78 | 79 | 80 | 81 | 82 | 82A |
|---|---|---|---|---|---|---|---|---|---|---|---|---|
| A | ASP | ASN | ALA | LYS | ASN | ILE | LEU | TYR | LEU | GLN | MET | SER |
| B | ASP | THR | SER | ALA | SER | THR | ALA | TYR | MET | GLU | LEU | SER |
| C | ASP | ASN | ALA | LYS | ASN | THR | LEU | TYR | LEU | GLN | MET | SER |

| | 82B | 82C | 83 | 84 | 85 | 86 | 87 | 88 | 89 | 90 | 91 | 92 |
|---|---|---|---|---|---|---|---|---|---|---|---|---|
| A | SER | LEU | ARG | SER | GLN | ASP | THR | ALA | MET | TYR | TYR | CYS |
| B | SER | LEU | ARG | SER | GLU | ASP | THR | ALA | VAL | TYR | TYR | CYS |
| C | SER | LEU | ARG | SER | GLN | ASP | THR | ALA | VAL | TYR | TYR | CYS |

| | 93 | 94 | 95 | 96 | 97 | 98 | 99 | 100 | 100A | 100B | 100C | 101 |
|---|---|---|---|---|---|---|---|---|---|---|---|---|
| A | ALA | ARG | VAL | TYR | TYR | TYR | GLY | SER | SER | TYR | PHE | ASP |
| B | ALA | ARG | | | | | | | | | | |
| C | ALA | ARG | VAL | TYR | TYR | TYR | GLY | SER | SER | TYR | PHE | ASP |

| | 102 | 103 | 104 | 105 | 106 | 107 | 108 | 109 | 110 | 111 | 112 | 113 |
|---|---|---|---|---|---|---|---|---|---|---|---|---|
| A | TYR | TRP | GLY | GLN | GLY | THR | THR | LEU | THR | VAL | SER | SER |
| B | | TRP | GLY | GLU | GLY | THR | LEU | VAL | THR | VAL | SER | SER |
| C | TYR | TRP | GLY | GLN | GLY | THR | LEU | VAL | THR | VAL | SER | SER |

FIGURE 10: VARIABLE REGION OF THE LIGHT OF IOR-CEA 1.

|   | 1 | 2 | 3 | 4 | 5 | 6 | 7 | 8 | 9 | 10 | 11 | 12 |
|---|---|---|---|---|---|---|---|---|---|---|---|---|
| A | ASP | ILE | GLN | MET | THR | GLN | SER | PRO | LYS | PHE | SER | SER |
| B | ASP | ILE | GLN | MET | THR | GLN | SER | PRO | SER | THR | LEU | SER |
| C | ASP | ILE | GLN | MET | THR | GLN | SER | PRO | SER | THR | LEU | SER |

|   | 13 | 14 | 15 | 16 | 17 | 18 | 19 | 20 | 21 | 22 | 23 | 24 |
|---|---|---|---|---|---|---|---|---|---|---|---|---|
| A | THR | SER | VAL | GLY | ASP | ARG | VAL | SER | VAL | THR | CYS | LYS |
| B | ALA | SER | VAL | GLY | ASP | SER | ILE | THE | ILE | THR | CYS | |
| C | ALA | SER | VAL | GLY | ASP | ARG | VAL | SER | VAL | THR | CYS | LYS |

|   | 25 | 26 | 27 | 28 | 29 | 30 | 31 | 32 | 33 | 34 | 35 | 36 |
|---|---|---|---|---|---|---|---|---|---|---|---|---|
| A | ALA | SER | GLN | ASN | ALA | GLY | ILE | ASN | VAL | ALA | TRP | TYR |
| B | | | | | | | | | | | TRP | PHE |
| C | ALA | SER | GLN | ASN | ALA | GLY | ILE | ASN | VAL | ALA | TRP | TYR |

|   | 37 | 38 | 39 | 40 | 41 | 42 | 43 | 44 | 45 | 46 | 47 | 48 |
|---|---|---|---|---|---|---|---|---|---|---|---|---|
| A | GLN | GLN | LYS | PRO | GLY | GLN | SER | PRO | LYS | ALA | LEU | ILE |
| B | GLN | GLN | LYS | PRO | GLY | LYS | ALA | PRO | ASN | VAL | LEU | ILE |
| C | GLN | GLN | LYS | PRO | GLY | GLN | SER | PRO | LYS | ALA | LEU | ILE |

|   | 49 | 50 | 51 | 52 | 53 | 54 | 55 | 56 | 57 | 58 | 59 | 60 |
|---|---|---|---|---|---|---|---|---|---|---|---|---|
| A | TYR | SER | ALA | SER | SER | ARG | ASN | SER | GLY | VAL | PRO | ASP |
| B | TYR | | | | | | | | GLY | ILE | PRO | SER |
| C | TYR | SER | ALA | SER | SER | ARG | ASN | SER | GLY | ILE | PRO | SER |

|   | 61 | 62 | 63 | 64 | 65 | 66 | 67 | 68 | 69 | 70 | 71 | 72 |
|---|---|---|---|---|---|---|---|---|---|---|---|---|
| A | ARG | PHE | THR | GLY | SER | GLY | SER | GLY | THR | ASP | PHE | THR |
| B | ARG | PHE | SER | GLY | SER | GLY | SER | GLY | THR | GLU | PHE | THR |
| C | ARG | PHE | SER | GLY | SER | GLY | SER | GLY | THR | GLU | PHE | THR |

|   | 73 | 74 | 75 | 76 | 77 | 78 | 79 | 80 | 81 | 82 | 83 | 84 |
|---|---|---|---|---|---|---|---|---|---|---|---|---|
| A | LEU | THR | ILE | SER | ASN | VAL | GLN | SER | GLN | ASP | LEU | ALA |
| B | LEU | THR | VAL | ILE | ASN | LEU | GLN | SER | ASP | ASP | PHE | ALA |
| C | LEU | THR | VAL | ILE | ASN | LEU | GLN | SER | ASP | ASP | PHE | ALA |

|   | 85 | 86 | 87 | 88 | 89 | 90 | 91 | 92 | 93 | 94 | 95 | 95A |
|---|---|---|---|---|---|---|---|---|---|---|---|---|
| A | GLU | TYR | PHE | CYS | GLN | GLN | TYR | ASN | SER | TYR | PRO | LEU |
| B | THR | TYR | TYR | CYS | | | | | | | | |
| C | THR | TYR | TYR | CYS | GLN | GLN | TYR | ASN | SER | TYR | PRO | LEU |

|   | 96 | 97 | 98 | 99 | 100 | 101 | 102 | 103 | 104 | 105 | 106 | 107 |
|---|---|---|---|---|---|---|---|---|---|---|---|---|
| A | VAL | THR | PHE | GLY | ALA | GLY | THR | LYS | LEU | GLN | LEU | LYS |
| B | | | PHE | GLY | GLN | GLY | THR | LYS | VAL | LEU | ILE | LYS |
| C | VAL | THR | PHE | GLY | GLN | GLY | THR | LYS | LEU | GLN | LEU | LYS |

|   | 108 | 109 |
|---|---|---|
| A | ARG | THR |
| B | ARG | THR |
| C | ARG | THR |

SEQUENCE LISTING ( 1 ) GENERAL INFORMATION:

( i i i ) NUMBER OF SEQUENCES: 31

( 2 ) INFORMATION FOR SEQ ID NO: 1:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 1:

GGAAGCTTAG ACCGATGGGG CCTGTTGTTT TG    32

( 2 ) INFORMATION FOR SEQ ID NO: 2:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 2:

GGAAGCTTGA AGATGGATAC AGTTGGTGCA GC    32

( 2 ) INFORMATION FOR SEQ ID NO: 3:

( i ) SEQUENCE CHARACTERISTICS:
        ( A ) LENGTH: 22 base pairs ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 3:

AGGTSMARCT GCAGSAGTCW GG 22

( 2 ) INFORMATION FOR SEQ ID NO: 4:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 4:

TTGAATTCCA GTGATGTTTT GATGACCCA 29

( 2 ) INFORMATION FOR SEQ ID NO: 5:

( i ) SEQUENCE CHARACTERISTICS:
        ( A ) LENGTH: 34 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 5:

TGAGGAGACG GTGACCGTGG TCCCTTGGCC CCAG 34

( 2 ) INFORMATION FOR SEQ ID NO: 6:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 6:

GACATTCAGC TGACCCA 17

( 2 ) INFORMATION FOR SEQ ID NO: 7:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 7:

GTTAGATCTC CAGTTTGGTG CT 22

( 2 ) INFORMATION FOR SEQ ID NO: 8:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 8:

GAAGCCCCAG GCTTCTTCAC TTCAGCCCCA GGCTG                    35

( 2 ) INFORMATION FOR SEQ ID NO: 9:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 9:

GTAAAACGAC GGCCAGT                                    17

( 2 ) INFORMATION FOR SEQ ID NO: 10:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 10:

CAGCCTGGGG CTGAAGTGAA GAAGCCTGGG GCTTCA                 36

( 2 ) INFORMATION FOR SEQ ID NO: 11:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 11:

ACTGGCCGTC GTTTTAC                                    17

( 2 ) INFORMATION FOR SEQ ID NO: 12:

( i ) SEQUENCE CHARACTERISTICS:
        ( A ) LENGTH: 65 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 12:

GCAGAGTCCT CAGATCTCAG GCTGCTGAGT TGCATGTAGA CTGTGCTGGT GGATTCGTCT    60

ACCGT    65

( 2 ) INFORMATION FOR SEQ ID NO: 13:

( i ) SEQUENCE CHARACTERISTICS:
    ( A ) LENGTH: 65 base pairs
    ( B ) TYPE: nucleic acid
    ( C ) STRANDEDNESS: unknown
    ( D ) TOPOLOGY: unknown ( i i ) MOLECULE TYPE: cDNA ( i i i ) HYPOTHETICAL: NO ( x i ) SEQUENCE DESCRIPTION: SEQ ID NO: 13:

ACGGTAGACG AATCCACCAG CACAGTCTAC ATGCAACTCA GCAGCCTGAG ATCTGAGGAC    60

TCTGC    65

( 2 ) INFORMATION FOR SEQ ID NO: 14:

( i ) SEQUENCE CHARACTERISTICS:
    ( A ) LENGTH: 116 amino acids
    ( B ) TYPE: amino acid
    ( C ) STRANDEDNESS: unknown
    ( D ) TOPOLOGY: unknown ( i i ) MOLECULE TYPE: protein ( i i i ) HYPOTHETICAL: NO ( x i ) SEQUENCE DESCRIPTION: SEQ ID NO: 14:

```
Asp Val Leu Met Thr Gln Ile Pro Leu Ser Leu Pro Val Ser Leu Gly
 1               5                  10                  15

Asp Gln Ala Ser Ile Ser Cys Arg Ser Gln Asn Ile Asn Ile Val
                20                  25                  30

His Ser Asn Gly Asn Thr Tyr Leu Asp Trp Tyr Leu Gln Lys Pro Gly
            35                  40                  45

Gln Ser Pro Asn Leu Leu Ile Tyr Lys Val Ser Asn Arg Phe Ser Gly
        50                  55                  60

Val Pro Asp Arg Phe Arg Gly Ser Gly Ser Gly Thr Asp Phe Thr Leu
 65                  70                  75                  80

Lys Ile Ser Arg Val Glu Ala Glu Asp Leu Gly Val Tyr Tyr Cys Phe
                 85                  90                  95

Gln Tyr Ser His Val Pro Trp Thr Phe Gly Gly Gly Thr Lys Leu Glu
             100                 105                 110

Ile Lys Arg Ala
         115
```

( 2 ) INFORMATION FOR SEQ ID NO: 15:

( i ) SEQUENCE CHARACTERISTICS:
    ( A ) LENGTH: 123 amino acids
    ( B ) TYPE: amino acid
    ( C ) STRANDEDNESS: unknown
    ( D ) TOPOLOGY: unknown ( i i ) MOLECULE TYPE: protein ( i i i ) HYPOTHETICAL: NO ( x i ) SEQUENCE DESCRIPTION: SEQ ID NO: 15:

```
Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Asn Tyr
             20                  25                  30

Tyr Ile Tyr Trp Val Lys Gln Arg Pro Gly Gln Gly Leu Glu Trp Ile
         35                  40                  45

Gly Gly Ile Asn Pro Thr Ser Gly Gly Ser Asn Phe Asn Glu Lys Phe
         50                  55                  60

Lys Thr Lys Ala Thr Leu Thr Val Asp Glu Ser Ser Thr Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gln Gly Leu Trp Phe Asp Ser Asp Gly Arg Gly Phe Asp Phe
                100                 105                 110

Trp Gly Gln Gly Thr Thr Leu Thr Val Ser Ser
             115                 120
```

( 2 ) INFORMATION FOR SEQ ID NO: 16:

( i ) SEQUENCE CHARACTERISTICS:
      ( A ) LENGTH: 87 amino acids
      ( B ) TYPE: amino acid
      ( C ) STRANDEDNESS: unknown
      ( D ) TOPOLOGY: unknown ( i i ) MOLECULE TYPE: protein ( i i i ) HYPOTHETICAL: NO ( x i ) SEQUENCE DESCRIPTION: SEQ ID NO: 16:

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Trp Val
             20                  25                  30

Arg Gln Ala Pro Gly Gln Gly Leu Glu Trp Met Gly Arg Val Thr Met
         35                  40                  45

Thr Arg Asp Thr Ser Thr Ser Thr Val Tyr Met Glu Leu Ser Ser Leu
 50                  55                  60

Arg Ser Glu Asp Thr Ala Val Tyr Tyr Cys Ala Arg Trp Gly Gln Gly
 65                  70                  75                  80

Thr Leu Val Thr Val Ser Ser
                 85
```

( 2 ) INFORMATION FOR SEQ ID NO: 17:

( i ) SEQUENCE CHARACTERISTICS:
      ( A ) LENGTH: 123 amino acids
      ( B ) TYPE: amino acid
      ( C ) STRANDEDNESS: unknown
      ( D ) TOPOLOGY: unknown ( i i ) MOLECULE TYPE: protein ( i i i ) HYPOTHETICAL: NO ( x i ) SEQUENCE DESCRIPTION: SEQ ID NO: 17:

```
Gln Val Gln Leu Gln Gln Pro Gly Ala Glu Val Lys Lys Pro Gly Ala
 1               5                  10                  15

Ser Val Lys Leu Ser Cys Lys Ala Ser Gly Tyr Thr Phe Thr Asn Tyr
             20                  25                  30

Tyr Ile Tyr Trp Val Lys Gln Arg Pro Gly Gln Gly Leu Glu Trp Ile
         35                  40                  45
```

Gly Gly Ile Asn Pro Thr Ser Gly Gly Ser Asn Phe Asn Glu Lys Phe
            50                  55                  60

Lys Thr Lys Ala Thr Leu Thr Val Asp Glu Ser Thr Ser Thr Val Tyr
65                      70                  75                  80

Met Gln Leu Ser Ser Leu Arg Ser Glu Asp Ser Ala Val Tyr Tyr Cys
                    85                  90                  95

Thr Arg Gln Gly Leu Trp Phe Asp Ser Asp Gly Arg Gly Phe Asp Phe
                100                 105                 110

Trp Gly Gln Gly Thr Thr Leu Thr Val Ser Ser
                115                 120

( 2 ) INFORMATION FOR SEQ ID NO: 18:

( i ) SEQUENCE CHARACTERISTICS:
      ( A ) LENGTH: 113 amino acids
      ( B ) TYPE: amino acid
      ( C ) STRANDEDNESS: unknown
      ( D ) TOPOLOGY: unknown ( i i ) MOLECULE TYPE: protein ( i i i ) HYPOTHETICAL: NO ( x i ) SEQUENCE DESCRIPTION: SEQ ID NO: 18:

Asp Val Leu Met Thr Gln Ile Pro Leu Ser Leu Pro Val Ser Leu Gly
1                   5                   10                  15

Asp Gln Ala Ser Ile Ser Cys Arg Ser Ser Gln Asn Ile Val His Ser
                20                  25                  30

Asn Gly Asn Thr Tyr Leu Asp Trp Tyr Leu Gln Lys Pro Gly Gln Ser
                35                  40                  45

Pro Asn Leu Leu Ile Tyr Lys Val Ser Asn Arg Phe Ser Gly Val Pro
        50                  55                  60

Asp Arg Phe Arg Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Tyr
                85                  90                  95

Ser His Val Pro Trp Thr Phe Gly Gly Gly Thr Lys Leu Glu Ile Lys
                100                 105                 110

Arg ( 2 ) INFORMATION FOR SEQ ID NO: 19:

( i ) SEQUENCE CHARACTERISTICS:
      ( A ) LENGTH: 81 amino acids
      ( B ) TYPE: amino acid
      ( C ) STRANDEDNESS: unknown
      ( D ) TOPOLOGY: unknown ( i i ) MOLECULE TYPE: protein ( i i i ) HYPOTHETICAL: NO ( x i ) SEQUENCE DESCRIPTION: SEQ ID NO: 19:

Asp Val Val Met Thr Gln Ser Pro Leu Ser Leu Pro Val Thr Leu Gly
1                   5                   10                  15

Gln Pro Ala Ser Ile Ser Cys Trp Phe Gln Gln Arg Pro Gly Gln Ser
                20                  25                  30

Pro Arg Arg Leu Ile Tyr Gly Val Pro Asp Arg Phe Arg Gly Ser Gly
                35                  40                  45

Ser Gly Thr Asp Phe Thr Leu Lys Ile Ser Arg Val Glu Ala Glu Asp
        50                  55                  60

```
Val  Gly  Val  Tyr  Tyr  Cys  Phe  Gly  Gln  Gly  Thr  Lys  Val  Glu  Ile  Lys
65                  70                      75                          80

Arg
```

( 2 ) INFORMATION FOR SEQ ID NO: 20:

( i ) SEQUENCE CHARACTERISTICS:
        ( A ) LENGTH: 119 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( x i ) SEQUENCE DESCRIPTION: SEQ ID NO: 20:

```
Glu  Val  Lys  Leu  Val  Gln  Ser  Gly  Gly  Gly  Leu  Val  Lys  Pro  Gly  Gly
1                   5                       10                          15

Ser  Leu  Lys  Leu  Ser  Cys  Ala  Ala  Ser  Gly  Phe  Lys  Phe  Ser  Arg  Tyr
               20                       25                      30

Ala  Met  Ser  Trp  Val  Arg  Gln  Thr  Pro  Glu  Lys  Arg  Leu  Glu  Trp  Val
          35                       40                      45

Ala  Thr  Ile  Ser  Ser  Gly  Gly  Ser  Ser  His  Leu  Leu  Ser  Arg  Gln  Cys
     50                       55                      60

Glu  Gly  Arg  Phe  Thr  Ile  Ser  Arg  Asp  Asn  Val  Lys  Asn  Thr  Leu  Tyr
65                       70                      75                      80

Leu  Gln  Met  Ser  Ser  Leu  Arg  Ser  Glu  Asp  Thr  Ala  Met  Tyr  Tyr  Cys
                85                       90                      95

Ala  Arg  Arg  Asp  Tyr  Asp  Leu  Asp  Tyr  Phe  Ala  Ser  Trp  Gly  Gln  Gly
               100                      105                     110

Thr  Thr  Leu  Thr  Val  Ser  Ser
               115
```

( 2 ) INFORMATION FOR SEQ ID NO: 21:

( i ) SEQUENCE CHARACTERISTICS:
        ( A ) LENGTH: 87 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( x i ) SEQUENCE DESCRIPTION: SEQ ID NO: 21:

```
Glu  Val  Gln  Leu  Leu  Glu  Ser  Gly  Gly  Gly  Leu  Val  Gln  Pro  Gly  Gly
1                   5                       10                          15

Ser  Leu  Arg  Leu  Ser  Cys  Ala  Ala  Ser  Gly  Phe  Thr  Phe  Ser  Trp  Val
               20                       25                      30

Arg  Gln  Ala  Pro  Gly  Lys  Gly  Leu  Glu  Trp  Val  Ser  Arg  Phe  Thr  Ile
          35                       40                      45

Ser  Arg  Asp  Asn  Ser  Lys  Asn  Thr  Leu  Tyr  Leu  Gln  Met  Asn  Ser  Leu
     50                       55                      60

Arg  Ala  Glu  Asp  Thr  Ala  Val  Tyr  Tyr  Cys  Ala  Lys  Trp  Gly  Gln  Gly
65                       70                      75                      80

Thr  Leu  Val  Thr  Val  Ser  Ser
                    85
```

( 2 ) INFORMATION FOR SEQ ID NO: 22:

-continued ( i ) SEQUENCE CHARACTERISTICS:
    ( A ) LENGTH: 119 amino acids
    ( B ) TYPE: amino acid
    ( C ) STRANDEDNESS: unknown
    ( D ) TOPOLOGY: unknown ( i i ) MOLECULE TYPE: protein ( i i i ) HYPOTHETICAL: NO ( x i ) SEQUENCE DESCRIPTION: SEQ ID NO: 22:

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ser Thr Ile Ser Ser Gly Gly Ser Ser His Leu Leu Ser Arg Gln Cys
    50                  55                  60

Glu Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Ala Ser Trp Gly Gln Gly
            100                 105                 110

Thr Leu Val Thr Val Ser Ser
            115

( 2 ) INFORMATION FOR SEQ ID NO: 23:

( i ) SEQUENCE CHARACTERISTICS:
        ( A ) LENGTH: 110 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( x i ) SEQUENCE DESCRIPTION: SEQ ID NO: 23:

Asp Ile Val Met Thr Gln Asp Gln Lys Phe Met Ser Thr Ser Val Gly
1               5                   10                  15

Asp Arg Val Ser Val Thr Cys Lys Ala Ser Gln Asn Ala Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Ser Arg Asn Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Val Thr Phe Gly Ala Gly Thr Lys Leu Glu Leu Lys Arg Ala
            100                 105                 110

( 2 ) INFORMATION FOR SEQ ID NO: 24:

( i ) SEQUENCE CHARACTERISTICS:
        ( A ) LENGTH: 82 amino acids
        ( B ) TYPE: amino acid
        ( C ) STRANDEDNESS: unknown ( D ) TOPOLOGY: unknown ( i i ) MOLECULE TYPE: protein ( i i i ) HYPOTHETICAL: NO ( x i ) SEQUENCE DESCRIPTION: SEQ ID NO: 24:

```
Glu Ile Val Met Thr Gln Ser Pro Ala Thr Leu Ser Val Ser Pro Gly
1               5                   10                  15
Glu Arg Ala Thr Leu Ser Cys Trp Tyr Gln Gln Lys Pro Gly Gln Pro
            20                  25                  30
Pro Arg Leu Leu Ile Tyr Gly Ile Pro Ala Arg Phe Ser Gly Ser Gly
        35                  40                  45
Ser Gly Thr Glu Phe Thr Leu Thr Ile Ser Arg Leu Gln Ser Glu Asp
    50                  55                  60
Phe Ala Val Tyr Tyr Cys Phe Gly Gln Gly Thr Arg Val Glu Ile Lys
65                  70                  75                  80
Arg Glu
```

( 2 ) INFORMATION FOR SEQ ID NO: 25:

( i ) SEQUENCE CHARACTERISTICS:
        ( A ) LENGTH: 110 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( x i ) SEQUENCE DESCRIPTION: SEQ ID NO: 25:

```
Asp Ile Val Met Thr Gln Asp Gln Lys Phe Met Ser Thr Ser Val Gly
1               5                   10                  15
Asp Arg Val Ser Val Thr Cys Lys Ala Ser Gln Asn Ala Gly Thr Asn
            20                  25                  30
Val Ala Trp Tyr Gln Gln Lys Pro Gly Gln Ser Pro Lys Ala Leu Ile
        35                  40                  45
Tyr Ser Ala Ser Ser Arg Asn Ser Gly Val Pro Ala Arg Phe Ser Gly
    50                  55                  60
Ser Gly Ser Gly Thr Asp Phe Thr Leu Thr Ile Ser Asn Val Gln Ser
65                  70                  75                  80
Glu Asp Phe Ala Val Tyr Tyr Cys Gln Gln Tyr Asn Ser Tyr Pro Leu
                85                  90                  95
Val Thr Phe Gly Ala Gly Thr Lys Leu Glu Leu Lys Arg Ala
                100                 105                 110
```

( 2 ) INFORMATION FOR SEQ ID NO: 26:

( i ) SEQUENCE CHARACTERISTICS:
        ( A ) LENGTH: 120 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( x i ) SEQUENCE DESCRIPTION: SEQ ID NO: 26:

```
Gln Pro Lys Leu Leu Glu Ser Gly Gly Asp Leu Val Lys Pro Glu Ala
1               5                   10                  15
Ser Leu Asn Cys Ser Cys Ala Val Ser Gly Phe Pro Phe Asn Arg Tyr
```

|   | 20 |   |   |   |   | 25 |   |   |   |   | 30 |   |   |   |
|---|---|---|---|---|---|---|---|---|---|---|---|---|---|---|
| Ala | Met | Ser<br>35 | Trp | Val | Leu | Gln | Thr<br>40 | Pro | Glu | Lys | Arg | Leu<br>45 | Glu | Trp | Val |
| Ala | Phe<br>50 | Ile | Ser | Ser | Asp | Asp<br>55 | Gly | Ile | Ala | Tyr | Tyr<br>60 | Ala | Glu | Ser | Lys |
| Gly<br>65 | Tyr | Arg | Phe | Thr | Ile<br>70 | Ser | Arg | Asp | Asn | Ala<br>75 | Lys | Asn | Ile | Leu | Tyr<br>80 |
| Leu | Gln | Met | Ser | Ser<br>85 | Leu | Arg | Ser | Gln | Asp<br>90 | Thr | Ala | Met | Tyr | Tyr<br>95 | Cys |
| Ala | Arg | Val | Tyr | Tyr<br>100 | Tyr | Gly | Ser | Ser<br>105 | Tyr | Phe | Asp | Tyr | Trp<br>110 | Gly | Gln |
| Gly | Thr | Thr<br>115 | Leu | Thr | Val | Ser | Ser<br>120 |

( 2 ) INFORMATION FOR SEQ ID NO: 27:

( i ) SEQUENCE CHARACTERISTICS:
        ( A ) LENGTH: 86 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( x i ) SEQUENCE DESCRIPTION: SEQ ID NO: 27:

| Gln<br>1 | Val | Gln | Leu | Val<br>5 | Gln | Ser | Gly | Ala | Glu<br>10 | Val | Lys | Lys | Pro | Gly<br>15 | Ala |
|---|---|---|---|---|---|---|---|---|---|---|---|---|---|---|---|
| Ser | Leu | Lys | Val<br>20 | Ser | Cys | Lys | Ala | Ser<br>25 | Gly | Tyr | Phe | Thr | Trp<br>30 | Val | Arg |
| Gln | Ala | Pro | Gly<br>35 | Gln | Arg | Leu | Glu | Trp<br>40 | Met | Gly | Arg | Val | Thr<br>45 | Ile | Thr |
| Arg | Asp | Thr<br>50 | Ser | Ala | Ser | Thr<br>55 | Ala | Tyr | Met | Glu | Leu<br>60 | Ser | Ser | Leu | Arg |
| Ser<br>65 | Glu | Asp | Thr | Ala | Val<br>70 | Tyr | Tyr | Cys | Ala | Arg<br>75 | Trp | Gly | Glu | Gly | Thr<br>80 |
| Leu | Val | Thr | Val | Ser<br>85 | Ser |

( 2 ) INFORMATION FOR SEQ ID NO: 28:

( i ) SEQUENCE CHARACTERISTICS:
        ( A ) LENGTH: 120 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( x i ) SEQUENCE DESCRIPTION: SEQ ID NO: 28:

| Gln<br>1 | Val | Gln | Leu | Val<br>5 | Gln | Ser | Gly | Ala | Glu<br>10 | Leu | Val | Lys | Pro | Gly<br>15 | Ala |
|---|---|---|---|---|---|---|---|---|---|---|---|---|---|---|---|
| Ser | Leu | Asn | Cys<br>20 | Ser | Cys | Ala | Val | Ser<br>25 | Gly | Phe | Pro | Phe | Asn<br>30 | Arg | Tyr |
| Ala | Met | Ser<br>35 | Trp | Val | Leu | Gln | Thr<br>40 | Pro | Glu | Lys | Arg | Leu<br>45 | Glu | Trp | Val |
| Ala | Phe<br>50 | Ile | Ser | Ser | Asp | Asp<br>55 | Gly | Ile | Ala | Tyr | Tyr<br>60 | Ala | Glu | Ser | Lys |

```
Gly Tyr Arg Phe Thr Ile Ser Arg Asp Asn Ala Lys Asn Thr Leu Tyr
65                  70                  75                  80

Leu Gln Met Ser Ser Leu Arg Ser Gln Asp Thr Ala Val Tyr Tyr Cys
                85                  90                  95

Ala Arg Val Tyr Tyr Tyr Gly Ser Ser Tyr Phe Asp Tyr Trp Gly Gln
            100                 105                 110

Gly Thr Leu Val Thr Val Ser Ser
            115                 120
```

(2) INFORMATION FOR SEQ ID NO: 29:

(i) SEQUENCE CHARACTERISTICS:
      (A) LENGTH: 110 amino acids
      (B) TYPE: amino acid
      (C) STRANDEDNESS: unknown
      (D) TOPOLOGY: unknown (ii) MOLECULE TYPE: protein (iii) HYPOTHETICAL: NO (xi) SEQUENCE DESCRIPTION: SEQ ID NO: 29:

```
Asp Ile Gln Met Thr Gln Ser Pro Lys Phe Ser Ser Thr Ser Val Gly
1               5                   10                  15

Asp Arg Val Ser Val Thr Cys Lys Ala Ser Gln Asn Ala Gly Ile Asn
            20                  25                  30

Val Ala Trp Tyr Gln Gln Lys Pro Gly Gln Ser Pro Lys Ala Leu Ile
            35                  40                  45

Tyr Ser Ala Ser Ser Arg Asn Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Gln Asp Leu Ala Glu Tyr Phe Cys Gln Gln Tyr Asn Ser Tyr Pro Leu
                85                  90                  95

Val Thr Phe Gly Ala Gly Thr Lys Leu Gln Leu Lys Arg Thr
            100                 105                 110
```

(2) INFORMATION FOR SEQ ID NO: 30:

(i) SEQUENCE CHARACTERISTICS:
      (A) LENGTH: 82 amino acids
      (B) TYPE: amino acid
      (C) STRANDEDNESS: unknown
      (D) TOPOLOGY: unknown (ii) MOLECULE TYPE: protein (iii) HYPOTHETICAL: NO (xi) SEQUENCE DESCRIPTION: SEQ ID NO: 30:

```
Asp Ile Gln Met Thr Gln Ser Pro Ser Thr Leu Ser Ala Ser Val Gly
1               5                   10                  15

Asp Ser Ile Thr Ile Thr Cys Trp Phe Gln Gln Lys Pro Gly Lys Ala
            20                  25                  30

Pro Asn Val Leu Ile Tyr Gly Ile Pro Ser Arg Phe Ser Gly Ser Gly
            35                  40                  45

Ser Gly Thr Glu Phe Thr Leu Thr Val Ile Asn Leu Gln Ser Asp Asp
50                  55                  60

Phe Ala Thr Tyr Tyr Cys Phe Gly Gln Gly Thr Lys Val Leu Ile Lys
65                  70                  75                  80

Arg Thr
```

( 2 ) INFORMATION FOR SEQ ID NO: 31:

( i ) SEQUENCE CHARACTERISTICS:
       ( A ) LENGTH: 110 amino acids
       ( B ) TYPE: amino acid
       ( C ) STRANDEDNESS: unknown
       ( D ) TOPOLOGY: unknown ( i i ) MOLECULE TYPE: protein ( i i i ) HYPOTHETICAL: NO ( x i ) SEQUENCE DESCRIPTION: SEQ ID NO: 31:

```
Asp Ile Gln Met Thr Gln Ser Pro Ser Thr Leu Ser Ala Ser Val Gly
 1               5                  10                  15
Asp Arg Val Ser Val Thr Cys Lys Ala Ser Gln Asn Ala Gly Ile Asn
             20                  25              30
Val Ala Trp Tyr Gln Gln Lys Pro Gly Gln Ser Pro Lys Ala Leu Ile
         35              40              45
Tyr Ser Ala Ser Ser Arg Asn Ser Gly Ile Pro Ser Arg Phe Ser Gly
     50              55              60
Ser Gly Ser Gly Thr Glu Phe Thr Leu Thr Val Ile Asn Leu Gln Ser
 65              70              75                          80
Asp Asp Phe Ala Thr Tyr Tyr Cys Gln Gln Tyr Asn Ser Tyr Pro Leu
                 85              90              95
Val Thr Phe Gly Gln Gly Thr Lys Leu Gln Leu Lys Arg Thr
             100             105             110
```

METHOD FOR OBTAINING MODIFIED IMMUNOGLOBULINS WITH REDUCED IMMUNOGENICITY OF MURINE ANTIBODY VARIABLE DOMAINS, COMPOSITIONS CONTAINING THEM

FIELD OF THE INVENTION

The present invention is related to the field of immunology, in particular to a method for obtaining modified immunoglobulins with reduced immunogenicity of murine antibody variable domains and compositions containing them.

BACKGROUND OF THE INVENTION

The immune system builds antibodies that bind to a vast range of antigens with high avidity and specificity, and trigger effector mechanisms. Antibodies have been used in medicine as diagnostic and therapeutic agents, and their potential has been successively enhanced with the advent of new technologies.

Hybridoma technology allowed isolation of cell lines secreting antibodies of a single specificity (Köhler G., Milsrein C. (1975) Nature (London) 256, 495–497), and gene technology has allowed the construction of a range of engineered antibodies from hybridomas.

Engineering of antibodies is facilitated by their domain structure and may further improve the utility of many antibodies by the acquisition or loss of some of their properties. The antigen-binding properties of the antibody provide the recognition function and this can be combined with to one or more of a number of effector agents. The combination of these two features must then be tested against the criteria of efficacy, specificity and immunogenicity.

Monoclonal antibody producing hybridomas have been most readily obtained from immunized rodents. At present, the use of several murine monoclonal antibodies has been widespreaded for the imaging and treatment of malignancy, prophylactic administration to guard against toxic shock, modification of graft rejection episodes, and to temper acute inflammatory reactions.

In most of the cases where rodent antibodies have been used for therapy, the recipients have elicited an immune response directed towards the antibodies themselves. Such reactions have limited the duration and effectiveness of the therapy.

Development of similar reagents from human sources has been frustated, although several options exist, using for example SCID-hu mice, in vitro immunization, recombinatorial libraries, or some useful combination of these. Because there are many well-characterized rodent monoclonal antibodies already available which might be used in the clinic if the immune response could be abolished, the production of engineered antibodies has received much attention.

Engineered antibodies have been designed to replace as much as possible of the xenogeneic sequences with the equivalent human sequence. Among the genetically engineered antibodies are chimaeric antibodies in which segments from immunoglobulins from diverse species are joined together.

Initially, chimaeric antibodies were constructed containing the rodent variable regions fused to human constant domains. Particularly mouse/human chimaeric antibodies are potentially useful for immunotherapy for they should exhibit the same specificity but reduced immunogenicity compared to their murine counterparts. The following references describe chimaeric antibody technology: Lobuglio et al, Proc. Natl. Acad. Sci. USA 86: 4220–4224 (1989); U.S. Pat. No. 4,816,567; PCT International Publication No. WO 87/02671 published May 7, 1987; European Patent Publication No. 255,694 published Feb. 10, 1988; European Patent Publication No. 274,394 published Jul. 13, 1988; European Patent Publication No. 323,806 published Jul. 12, 1989; PCT International Publication No. WO 89/00999 published Feb. 9, 1989; European Patent Publication No. 327,000 published Aug. 9, 1989; European Patent Publication No. 328,404 published Aug. 16, 1989; and European patent Publication No. 332,424 published Sep. 12, 1989.

It is worth noting that even the replacement of the Constant regions with human equivalents may not effectively reduce their immunogenicity. Still approximately half of the recipients mounted an immune response to the rodent variable regions. Subsequently, rodent antibodies have been extensively manipulated to resemble more fully human antibodies.

Further reduction in the immunogenicity of chimaeric antibodies has been achieved by grafting only the complementarity determining regions (CDRs) from the rodent monoclonal antibody onto human framework regions (FRs) prior to its subsequent fusion with an appropriate constant domain (Jones et al, Nature 321: 522–525 (1986)). This procedure to accomplish CDR-grafting often results in imperfectly humanized antibodies, for example, the resultant antibody has either lost affinity or in an attempt to retain its original affinity a number of the murine framework residues have replaced the corresponding ones of the chosen human framework (Winter, European Patent Application, Publication No. 239,400; Riechmann et al, Nature 332: 323–327 (1988)).

Strategies have has been developed with the objective of identifying the minimum number of residues for transfer to achieve a useful binding affinity with the least potential consequences on immunogenicity. However, it has emerged that each of these strategies has only been successful to some degree in the reconstitution of parental affinity.

The ligand binding characteristics of an antibody combining site are determined primarily by the structure and relative disposition of the CDRs, although some neighbouring framework residues also have been found to be involved in antigen binding (Davies et al, Ann. Rev. Biochem. 59: 439–473 (1990)). Thus, the fine specificity of an antibody can be preserved if its CDR structures and some of the neighbouring residues, their interaction with each other, and their interaction with the rest of the variable domains can be strictly maintained.

A further procedure for the humanization of an antibody has been suggested by Padlan (Padlan, European Patent Application, Publication No. 0 519 596 A1; Padlan, Molecular Immunology 28: 489–498 (1991)). It is based on the fact that the antigenicity of a protein is dependent on the nature of its surface, and a number of the solvent-accessible residues in the rodent variable region are substituted by residues from a human antibody. The locations of these residues are identified from an inspection of the high resolution X-ray structures of the human antibody KOL and the murine antibody J539. The choice of the human surface residues is arrived at by identifying the most homologous antibody sub-group.

The nature of the protein surface is important for its recognition and internalization by antigen-processing cells, specifically by antigen-specific B-cells. In addition, the recognition of specific linear sequences by T-cells is also an important element in the immunogenicity of proteins.

Several groups have developed automated-computerized methods for the identification of sequence features and structural determinants that play a role in the MHC restriction of helper T-cell antigenic peptides (Bersofsky et al, J. Immunol. 138: 2213-2229 (1987), Elliott et al, J. Immunol. 138: 2949-2952 (1987), Reyes et al, J. Biol. Chem. 264: 12854-12858 (1989)). Using these algorithms, it has been possible to identify predicted T cell-presented peptides.

Analysis of antibodies of known atomic structure has elucidated relationships between the sequence and three-dimensional structure of antibody combining sites (Chothia et al, J. Biol. Chem. 196: 901-917 (1987)). These relationships imply that, except for the third region in the VH domains, binding site loops have one of a small number of main-chain conformations: "Canonical structures". The canonical structure formed in a particular loop is determined by its size and the presence of certain residues at key sites in both the loop and in framework regions.

An additional subset of framework residues has been defined as a "Vernier" zone, which may adjust CDR structure and fine-tune the fit to antigen (Foot et al, J. Mol. Biol. 224: 487-499 (1992)). Substitutions of these residues have been shown to be important to restoring the affinity in CDR grafted antibodies, so the Vernier zone has an obvious consequence for the design of humanized antibodies.

SUMMARY OF THE INVENTION

The invention provides a means of converting a monoclonal antibody of one mammalian species to a monoclonal antibody of another species. The invention is useful in predicting potential T-epitopes within the sequence of variable regions. The invention is useful in identifying the amino acid residues responsible for species specificity or immunogenicity within the sequence of the monoclonal antibody responsible of the T-immunogenicity. Another aspect of the invention is to judiciously replace the amino acid residues within the T-epitope sequences of one species with those of a second species so that the antibodies of the first species will not be immunogenic in the second species. A further aspect involves providing replacements only in the framework regions of the heavy and light chains and not in the complementarity determining regions; also the amino acids belonging to the Vernier zone and those involved in the canonical structures cannot be replaced. Another aspect involves providing novel DNA sequences incorporating the replacement amino acid residues. Another aspect involves providing a vector containing the DNA sequences for the altered antibody. Another aspect involves providing a eukaryotic or procaryotic host transformed with a vector containing the DNA sequence for the modified antibody.

A unique method is disclosed for identifying and replacing amino acid residues within T-cell antigenic sequences which converts immunoglobulin antigenicity of a first mammalian species to that of a second mammalian species. The method will simultaneously change immunogenicity and strictly preserve ligand binding properties. A judicious replacement of those amino acid residues within T-cell antigenic sequences of the variable regions, which are not involved in the three-dimensional structure, has no effect on the ligand binding properties but greatly alters immunogenicity.

BRIEF DESCRIPTION OF THE DRAWINGS

FIG. 1 Deduced amino acid sequence of (a) VK and (b) VH of murine R3 antibody. CDRs are underlined.

FIGS. 2 and 3 Analysis for the modification of the variable regions of heavy and light chains of antibody IOR-R3.

A: sequence of the variable region of the murine IOR-R3 monoclonal antibody.

B: sequence of the variable region of the most homologous human immunoglobulin.

C: sequence of the modified variable region of IOR-R3.

shading: predicted T-cell antigenic sequences.

underlined amino acid residues: amino acids involved in tertiary structure.

bold font: complementarity determining regions.

amino acid residues in boxes: proposed replacements.

The description is the same for both, heavy and light chains.

FIG. 4 Molecular model of the variable region of mAb R3 displayed as a ribbon. VH is on the right and is darker than VL. The model shows the side chain of murine residues that were mutated in order to humanize the predicted amphipatic segments.

FIG. 5 Detection of binding of the chimaeric and mutant R3 to EGF-R by RRA.

Antigen binding activity was assayed in different concentrations of purified murine R3 (-.-), chimaeric R3 (+) and mutant VHR3/muR3VK (*) and plotted as CPM of bound $^{125}$I-EGF against log of the concentration of each antibody. (concentration of IgG was quantitated by ELISA.)

FIG. 6 Immunization of monkeys with murine R3, chimaeric R3 and mutant R3.

ordinates: Absorbance at 405 nm.

abscises: number of days of blood collected.

The ELISA was performed as described in EXAMPLE 9. The arrows indicate the time of intravenous injection of 2 mg of each mAb. The serum dilution used was 1/10,000.

FIGS. 7 and 8 Analysis for the modification of the variable regions of heavy and light chains of antibody IOR-T1.

A: sequence of the variable region of the murine IOR-T1 monoclonal antibody.

B: sequence of the variable region of the most homologous human immunoglobulin.

C: sequence of the modified variable region of IOR-T1 antibody.

The symbols are the same as in FIG. 2. The description is the same for both, heavy and light chains.

FIGS. 9 and 10: Analysis for the modification of the variable regions of heavy and light chains of antibody IOR-CEA1.

A: sequence of the variable region of the murine IOR-CEA1 monoclonal antibody.

B: sequence of the variable region of the most homologous human immunoglobulin.

C: sequence of the modified variable region of IOR-CEA1 antibody.

The symbols are the same as in FIG. 2. The description is the same for both, heavy and light chains.

DETAILED DESCRIPTION OF THE INVENTION

The present invention relates to a procedure which simultaneously reduces immunogenicity of the rodent monoclonal antibody while preserving its ligand binding properties in its entirety. Since the antigenicity of an immunoglobulin is dependent on the presence of T-cell antigenic peptides within its sequence, the immunogenicity of a xenogenic or allogenic antibody could be reduced by replacing the residues included in the T-cell antigenic sequences which differ from those usually found in antibodies of another mammalian species.

The replacement of residues does not include those involved in the canonical structures or in the Vernier zone. This judicious replacement of residues has no effect on the structural determinants or on the interdomain contacts, thus, ligand binding properties should be unaffected as a consequence of alterations which are limited to the variable region framework residues.

(1) Analysis of Homology of Variable Regions

The present procedure makes use of the available sequence data for human antibody variable domains compiled by Kabat et al, "Sequences of proteins of Immunological Interest", Fifth edition, Bethesda, Md.; National Inst. of Health, 1994.

In the first step the variable domains of any heavy or light chain of a first animal species, e.g. the mouse, are compared with the corresponding variable domains of a second animal species, e.g. human. It is intended that this invention will allow the antigenic alteration of any animal species antibody.

The comparison is made by an automated-computerized method (PC-DOS HIBIO PROSIS 06-00, Hitachi). The most homologous human variable regions are then compared, residue for residue, to the corresponding murine regions. This will also define the human subgroup to which each mouse sequence most closely resembles.

(2) Prediction of T-epitopes

In the second step, the two homologous variable region sequences, mouse and human, are analysed for the prediction of T-antigenic sequences.

The algorithm AMPHI (Bersofsky et al, The Journal of Immunology 138: 2213–2229 (1987)) predicts α Helical sequences. The algorithm SOHHA predicts the strip of helix hydrophobicity (Elliott et al, J. Immunol. 138: 2949–2952 (1987)). These algorithms predict T-cell presented fragments of antigenic proteins.

(3) Analysis for Immunogenicity Reduction

Those residues in the mouse framework which differ from its human counterpart are replaced by the residues present in the human counterpart. This switching (replacement) occurs only with those residues which are in the T-antigenic sequences.

Finally, replacement of those residues responsible for the canonical structures or those involved in the Vernier zone could have a significant effect on the tertiary structure. Hence, they cannot be included in the replacement. Additional information about the influence of the proposed replacements on tertiary structure or the binding site could be obtained from a molecular model of the variable regions.

The molecular model can be built on a Silicon Graphics Iris 4D workstation running UNIX and using the molecular modeling package "QUANTA" (Polygen Corp.).

(4) Method for Constructing and Expressing the Altered Antibody

The following procedures are used to prepare recombinant DNA sequences which incorporate the CDRs of a first mammalian species, usually animal, e.g. murine mAb, both light and heavy chains, into a second mammalian species, preferably human, appearing frameworks that can be used to transfect mammalian cells for the expression of recombinant antibody less immunogenic and with the antigen specificity of the animal monoclonal antibody.

The present invention further comprises a method for constructing and expressing the modified antibody comprising:

a.-) mutagenesis and assembly of variable region domains including CDRs and FRs regions. The PCR-mutagenesis method (Kamman et al, Nucleic Acids Res. 17: 5404–5409 (1989)) is preferably used to introduce the changes at different positions.

b.-) preparation of an expression vector including one variable region and the corresponding human constant region which upon transfection into cells results in the secretion of protein sufficient for affinity and specificity determinations.

c.-) co-transfection of heavy and light chain expression vectors in appropriate cell lines.

After about 2 weeks, the cell supernatants are analyzed by ELISA for human IgG production. The samples are then analysed by any method for human IgG capable of binding to specific antigens.

The present invention provides a method for incorporating CDRs from animal monoclonal antibodies into frameworks which appear to be human immunoglobulin in nature so that the resulting recombinant antibody will be either weakly immunogenic or non-immunogenic when administered to humans. Preferably, the recombinant immunoglobulins will be recognized as self proteins when administered for therapeutic purpose. This method will render the recombinant antibodies useful as therapeutic agents because they will be either weakly immunogenic or non-immunogenic when administered to humans.

The invention is further contemplated to include the recombinant conversion of any animal monoclonal antibody into a recombinant human-appearing monoclonal antibody by providing that with a suitable framework region.

The invention is intended to include the conversion of any animal immunoglobulin to a human-appearing immunoglobulin. It is further intended that human-appearing immunoglobulin can contain either Kappa or Lambda light chains or be one of any of the following heavy chain isotypes (alpha, delta, epsilon, gamma and mu).

The following examples intend to illustrate the invention but not to limit the scope of the invention.

EXAMPLE 1

Murine Variable Region of R3 Monoclonal Antibody DNA Sequencing

Cytoplasmic RNA was extracted from about $10^6$ R3 (anti Epidermal growth Factor receptor) hybridoma cells as described by Faloro et al (Faloro, J. et al, Methods in Enzymology 65: 718–749, 1989).

The cDNA synthesis reaction consisted of 5 ug RNA, 50 mM Tris-HCl, pH 7.5, 75 mM KCl, 10 mM DTT, 3 mM $MgCl_2$, 25 pmol of CG2AFOR primer (5' GGAAGCTTA-GACCGATGGGGCCTGTTGTTTTG 3') for the heavy chain variable region or CK2FOR primer (5' GGAAGCT-TGAAGATGGATACAGTTGGTGCAGC 3') for the light chain variable region, 250 uM each of dATP, dTTP, dCTP, dGTP, 15 U ribonuclease inhibitor (RNA guard, Pharmacia) in a total volume of 50 ul. Samples were heated at 70° C. for 10 min and slowly cooled to 37° C. over a period of 30 min. Then, 100 units MMLV reverse transcriptase (BRL) were added and the incubation at 37° C. continued for 1 hour.

The VH and VK cDNAs were amplified using the PCR as described by Orlandi et al (Orlandi, R. et al, Proc. Natl. Acad. Sci. USA 86: 3833–3837, 1989). For PCR amplification of VH, DNA/primer mixtures consisted of 5 ul cDNA, 25 pmoles of CG2AFOR primer (5' GGAAGCTTA-GACCGATGGGGCCTGTTGTTTTG 3') and VH1BACK primer (5' AGGT(G/C)(A/C)A(A/G)CTGCAG(G/C)AGTC (A/T)GG 3').

For PCR amplification of VK, DNA/primers mixtures consisted of 5 ul cDNA and 25 pmoles of CK2FOR primer (5' GGAAGCTTGAAGATGGATACAGTTGGTGCAGC 3') and VK10BACK primer (5' TTGAATTCCAGTGAT-GTTTTGATGACCCA 3'). To these mixtures were added 2.5 mM each of dATP, dCTP, dTTP, and dGTP, 5 ul constituents of 10X buffer thermolase and 1 unit of Thermolase (IBI) in a final volume of 50 ul. Samples were subjected to 25 thermal cycles at 94° C., 30 sec; 50° C., 30 sec; 72° C., 1 min; and a last incubation for 5 min at 72° C. Amplified VH and VK DNA were purified on Prep. A Gene purification kit (BioRad).

The purified VH and VK cDNA were cloned into M13 vector. Clones were sequenced by the dideoxy method using T7 DNA Pol (Pharmacia). See FIG. 1.

EXAMPLE 2

Construction of Chimaeric Genes

We reamplified the cDNA by PCR using VH1BACK primer (5' AGGT(G/C)(A/C)A(A/G)CTGCAG(G/C)AGTC (A/T)GG 3') and VH1FOR primer (5' TGAGGAGACGGT-GACCGTGGTCCCTTGGCCCCAG 3') for VH and VK3BACK primer (5'GACATTCAGCTGACCCA 3') and VK3FOR primer (5' GTTAGATCTCCAGTTTGGTGCT 3') for VK. The amplified cDNAS were digested with PstI and BstEII for the VH gene or PvuII and BglII for the VK gene. The fragments were cloned into M13-VHPCR1 (digested with PstI and BstEII) or into M13-VKPCR1 (digested with PvuII and BclI). Details of vectors are given by Orlandi, R. et al, Proc. Natl. Acad. Sci. USA 86: 3833–3837, 1989. The M13VHPCR-R3 and M13VKPCR-R3 containing V gene inserts were identified directly by sequencing.

The VH gene together with the Ig heavy chain promoter, appropriate splicing sites and signal peptide sequences were excised from M13 vectors by digestion with HindIII and Bam HI and cloned into an expression vector (pSVgpt). A human IgG1 constant region (Takahashi, N. et al, Cell 29: 718–749, 1982) was then added as a BamHI fragment. The resultant construction was R3VH-pSVgpt. The construction of the R3VK-pSVhyg was essentially the same except that the gpt gene was replaced by the hygromicin resistance gene and a human Kappa chain constant region was added (Hieter, P. A. et al, Cell 22: 197–207, 1980).

EXAMPLE 3

Modification of the Variable Domain Sequences of IOR-R3 Murine Monoclonal Antibody to Humanize the Predicted T-cell Antigenic Sequences The variable region sequences of heavy and light chains of R3 were analyzed for T-cell antigenic sequences. It was made by using the computer algorithm AMPHI, which predicts segments of the sequences 11 amino acids in length with an amphipatic helix structure, that is have one side hydrophobic and one side hydrophilic which bind to MHC II molecules.

Within the variable domain sequence of the heavy chain were predicted 5 segments which are (using Kabat's numbering):

1. FR1 between amino acids 3–13.

2. FR1 between amino acids 8–20.
3. FR2 and CDR2 between amino acids 39–55.
4. FR3 between amino acids 74–84.
5. FR4 and CDR3 between amino acids 100c–110.

FIG. 2 shows the sequences corresponding to the heavy chain.

This murine sequence is compared with the immunoglobulin sequences included in the GeneBank and EMBL database. The most homologous human variable region sequence is determined and also the human subgroup to which the murine sequence most closely resembles is defined. In this case the human sequence found was a fetal immunoglobulin called HUMIGHVA, which variable region has 75% of homology with the FR regions of the murine immunoglobulin R3.

Both variable region sequences, human and murine are then compared, residue for residue, and those residues in FR regions which are not involved in the vernier zone or with the canonical structures are selected. Therefore they could be changed by those residues at the same position within the human sequence.

Finally, this analysis is enriched with computer modeling of the binding site. On the molecular model it is possible to define those replacements which will perturb the tertiary structure of the binding site.

For the heavy chain of murine R3 we propose 6 replacements:

1. LEU at position 11 by VAL
2. VAL at position 12 by LYS

With only these two replacements it is possible to disrupt the amphipatic helix and therefore the predicted T-epitope in the FR1.

3. SER at position 75 by THR
4. THR at position 76 by SER
5. ALA at position 78 by VAL
6. THR at position 83 by ARG In this case, with the replacements proposed in the FR3, it is humanized.

The T-cell antigenic sequence in the FR2 contains two PRO which is a very rare amino acid residue in most of the helical antigenic sites, so we propose that it is not a real T-cell epitope.

In the position 108 at the FR4 appears THR which is present in the same position in some human immunoglobulins, only residue 109 (LEU) is very rare in human, except for this point difference most of the predicted T-cell epitope is human, on this basis it does not need to be modified.

In FIG. 3 the analysis for the light chain of murine R3 is shown.

In the sequence only one amphipatic helix was predicted, between residue 52–63 corresponding to CDR2 and FR3, and in this region only one point difference exists between murine and human sequences, at position 63. No replacement is proposed, because this murine light chain should be non-immunogenic in human (see molecular modelling).

EXAMPLE 4

Molecular Modelling of mAb R3 VK and VH

A model of the variable regions of mouse mAb R3 was built using the molecular modeling program QUANTA/ CHARm 4.0 (Molecular Simulations Inc., 1994), running on a 150 MHz Silicon Graphics Indigo Extreme workstation. The VK and VH frameworks were built separately from Fab 26–10 (Jeffrey, P. D et al, Proc. Natl. Acad. Sci. USA 90, 10310, 1993) and Fab 36–71 (Strong, R. K. et al, Biochemistry 30, 3739, 1993), respectively. Fab 26–10 and mAb R3 have 92% homology in the VK frameworks and 88% homology in the whole VK region. The VH frameworks of Fab 36–71 and mAb R3 have 85% homology.

Coordinates were taken from the Brookhaven Protein Data Bank (entries IIGI and 6FAB). The frameworks of Fab 36–71 were fitted to the frameworks of Fab 26–10, matching only those residues that have been found to be often involved in the interface between the light and heavy variable regions (Chotia, C. et al, J. Mol. Biol. 186, 651, 1985). The VH domain of Fab 26–10 and the VK domain of Fab 36–71 were then deleted leaving the needed hybrid. Side-chain replacements were performed following the maximum overlap procedure (Snow, M. E. et al, Proteins 1, 267, 1986) and comparing, where possible, with other crystal structures.

The hypervariable regions of the R3-Variable Light (VL) domain (L1, L2 and L3) were built retaining the same main-chain conformations as in Fab 26–10, since the corresponding CDRs in both antibodies are highly homologous and belong to the same canonical structural groups (Chotia, C. et al, Nature 342, 877, 1989). In the VH domain of mAb R3, CDR H1 belongs to canonical structural group 1, as in Fab 36–71, so the main-chain torsion angles of the parent molecule were kept. CDR H2 corresponds to canonical structural group 2 and the main-chain conformation for this loop was taken from the Fv fragment 4D5 (entry 1FVC), which was selected among other highly resolved structures because of the good matching of its H2 loop base with the framework of Fab 36–71. For all the above mentioned loops comparisons with other CDRs from the Data Bank were made to orient the side chains.

To model CDR H3, which in mAb R3 was 14 amino acids long, a high temperature molecular dynamics was used for conformational sampling (Bruccoleri, R. E. et al, Biopolymers 29, 1847, 1990). First, the whole structure without CDR H3 was subjected to an energy minimization keeping residues H-94 and H-103 fixed and using harmonic constraints of 10 Kcal/(mole atom $A^2$) for main chain atoms. Then a loop was constructed with an arbitrary conformation starting from the two previously fixed amino acids. Those residues close to the framework were placed taking into consideration other crystal structures and the top part of the loop was built with an extended conformation avoiding strong steric interactions with the rest of the molecule. For the next modeling steps only CDR H3 and the neighbouring side chains within a distance of 5A° were permitted to move. An energy minimization was first carried out and then a molecular dynamics at 800K was run for 150 picoseconds. The time step for the run was set to 0.001 picosecond and coordinates were saved every 100 steps. The 120 lowest energy conformations from the dynamics run were extracted and subjected to an energy minimization in which all atoms in the structure were allowed to move. Several low-energy conformations were obtained and the one with the lowest energy was used in the subsequent analyses. Differences between murine and humanized variants of R3 antibody were individually modeled to investigate their possible influence on CDR conformation.

Amino acid replacements in positions 11, 12 (FR1) and 83 (FR3) in the heavy chain variable region are quite enough distant from the CDRs-FRs boundaries and should not have any influence on binding affinity. SER 75 residue is pointing to outside, thus the replacement by THR seems not to be important for binding capacity. By contrary THR 76 is accessible from the top of the molecule and could be involved in the interaction with the antigen. But the substitution of THR 76 by SER is a conservative change, leading to no major variations in binding affinity probably.

The replacement of ALA 78 by VAL should not require steric rearrangements. However VAL 78 could "push" forward ILE 34 (H!). In general, the proposed point mutations should not affect binding affinity according to the computer-aided molecular modelling study (FIG. 4).

The same analysis was done in the light chain variable region of IOR-R3, molecular modelling indicates it is not necessary to make any changes in this region.

EXAMPLE 5

Construction of Mutant Heavy Chain Variable Region of R3 by PCR Mutagenesis

The changes in the amino acids of mutant heavy chain variable region were constructed using PCR mutagenesis (Kammann, M. et al, Proc. Natl. Acad. Sci. USA 86, 4220–4224, 1989).

Briefly: Two amplification by PCR: the reaction mixture was: 0.5 ul the VH supernatant of single strand DNA cloned in M13, 25 pmoles mutagenic oligo 1 or 2, 25 pmoles mutagenic oligo 3 or 4 primers (See below the primers sequences). To these mixtures were added 2.5 mM each of dATP, dCTP, dTTP, and dGTP, 5 ul constituents of 10X Vent Polymerase buffer (NEB) and 1 unit of Vent DNA Polymerase (NEB) in a final volume of 50 ul. Samples were subjected to 12–15 thermal cycles at 94° C., 30 sec; 50° C., 30 sec; 75° C., 1 min; and a last incubation for 5 min at 75° C. The products of both PCRs are joined in a second PCR using the outside primers only (3 and 4). Amplified VH DNA was purified on Prep. A Gene purification kit (BioRad).

For the changes in the FR1 of LEU 11 and VAL 12 by VAL and LYS, respectively, the following primers were used:

Primer 1: 5' GAAGCCCCAGGCTTCTTCACTTCAGC-CCCAGGCTG 3'.
Primer 3: 5' GTAAAACGACGGCCAGT 3'.
These primers are combined in one PCR.
Primer 2: 5' CAGCCTGGGGCTGAAGTGAAGAAGC-CTGGGGCTTCA 3'
Primer 4: 5' ACTGGCCGTCGTTTTAC 3'
These primers are combined in one PCR.
Then, the products of both PCRs are combined in one PCR using primers 3 and 4.

For the changes in the FR3, SER 75, THR 76, VAL 78 and THR 86 by THR, SER, VAL and ARG, respectively, the following primers were designed:

Primer 1: 5' GCAGAGTCCTCAGATCTCAGGCTGCT-GAGTTGCATGTAGACTGTGCTGGTGGAT-TCGTCTACCGT 3'.
Primer 3: 5' GTAAAACGACGGCCAGT 3'.
These primers are combined in one PCR.
Primer 2: 5' ACGGTAGACGAATCCACCAGCA-CAGTCTACATGCAACTCAGCAGCCT-GAGATCTGAGGACTCTGC 3'
Primer 4: 5' ACTGGCCGTCGTTTTAC 3'.
These primers are combined in one PCR.
Then, the products of both PCRs are combined in one PCR using primers 3 and 4.

After mutagenesis VH genes were cloned in expression vectors (pSVgpt) yielding the plasmids R3 mut VH-pSVgpt.

EXAMPLE 6

Transfection of DNA into NSO Cells

Four ug of R3VH-pSVgpt and 8 ug R3VK-pSVhyg (chimaeric) or R3 mutant VH-pSVgpt and murine R3VKpSVhyg were linearized by digestion with PvuL. The DNAs were mixed together, ethanol precipitated and dissolved in 25 ul water. Approximately $10^7$ NSO cells (Rat myeloma NSO is a non-Ig secreting cell line) were grown to semiconfluency, harvested by centrifugation and resuspended in 0.5 ml DMEN together with the digested DNA in an electroporation single pulse of 170V at 960 uF (Gene-Pulser, Bio-Rad) and left in ice for a further 30 min. The cells were then put into 20 ml DMEN plus 10% fetal calf serum and allowed to recover for 24 hours. At this time the cells were distributed into a 96-well plate and selective medium applied, transfected clones were visible with the naked eyes 14 days later.

EXAMPLE 7

Quantification of IgG Production

The presence of human antibody in the medium of wells containing transfected clones was measured by ELISA. Microtiter plate wells were coated with goat anti-human IgG (heavy chain specific) antibodies (Sera-Lab). After washing with PBST (phosphate buffered saline containing 0.02% Tween 20, pH 7.5), 20 ul of culture medium diluted in 100 ul of PBST from the wells containing transfectants was added to each microtiter well for 1 hour at 37° C. The wells were then emptied, washed with PBST and either peroxidase-conjugated goat anti human kappa (light chain specific) region antibodies (Sera-Lab) were added and incubated at 37° C. for 1 hour, the wells were then emptied, washed with PBST and substrate buffer containing orthophenylenediamine added. Reactions were stopped after a few minutes by the addition of sulphuric acid and absorbance at 492 nm was measured.

EXAMPLE 8

EGF Receptor Radioligand Competition Assays

The determination of the affinity constant of the $^{125}$I-EGF binding to its receptor by murine R3, chimaeric and mutant by rupture of epitopes T antibodies was performed by a homogeneous Radio Receptor Analysis (RRA) with human placenta microsomal fraction (Macias, A. et al, Interferony Biotecnologia 2: 115–127, 1985).

Figure 5:
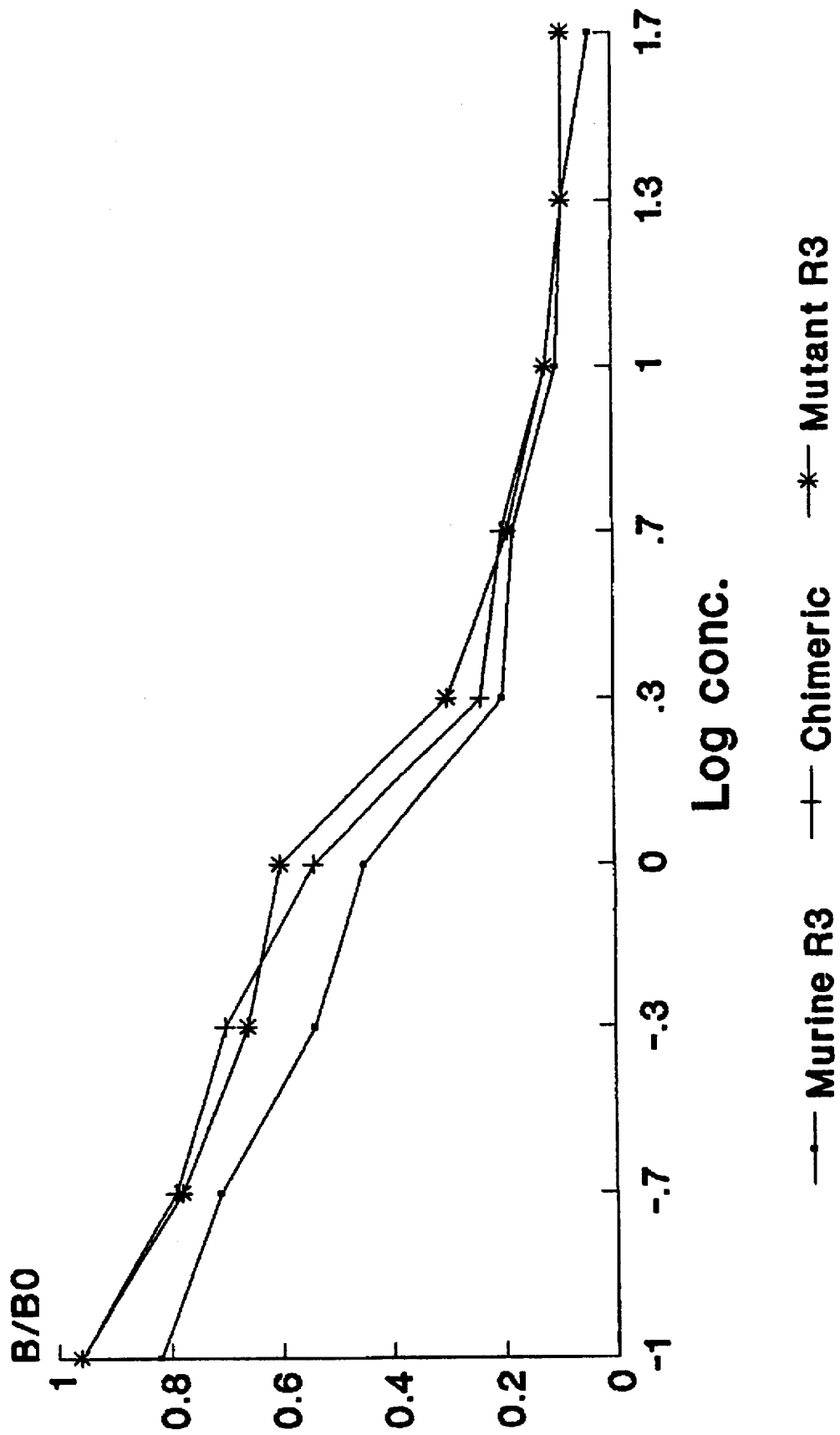

These chimaeric and mutant by rupture of epitopes T antibodies were assayed using this technique for its ability to bind to EGF-R (FIG. 5). Both antibodies bound to EGF-R with the same affinity as the original murine antibody ($10^{-9}$M), confirming that the correct mouse variable regions had been cloned and the new antibody isotype did not affect binding. Even more, the changes in the mutant antibody did not affect binding to the antigen.

EXAMPLE 9

Immunization of Cercopithecus Aethiops Monkeys with the Murine, Chimaeric and VH Mutant Antibodies Three treatment groups with two Cercopithecus aethiops monkeys in each group were immunized with murine R3 mAb, chimaeric R3 antibody and mutant VH R3 antibody, respectively. All the groups were immunized subcutaneously on days 0, 14, 28 and 42, with 2 mg of antibody adsorbed into 5 mg of aluminum hydroxide.

Blood was collected prior to the first immunization and one week later of each immunization, from all the groups, and the serum was obtained from each sample, and kept at −20° C. The titer of antibodies against the murine R3 mAb was determined by an ELISA technique.

Costar plates (Inc, high binding) were coated with murine R3 monoclonal antibody at a concentration of 10 ug/ml in bicarbonate buffer (pH 9.6) and incubated overnight. Thereafter, the plates were washed with PBST, were blocked with the same buffer containing 1% BSA during one hour at room temperature.

The washing step was repeated and 50 ul/well of the different serum dilutions were added. After incubating for 2 hours at 37° C., the plates were washed again and incubated 1 hour at 37° C. with alkaline phosphated conjugated goat anti-human total or anti-human IgG Fc region specific antiserum (Sigma, Inc). After washing with PBST the wells were incubated with 50 ul of substrate buffer (1 mg/ml of p-nitrophenylphosphate diluted in diethanolamine buffer (pH 9.8)). Absorbance at 405 nm in an ELISA reader (Organon Teknika, Inc).

Figure 6:
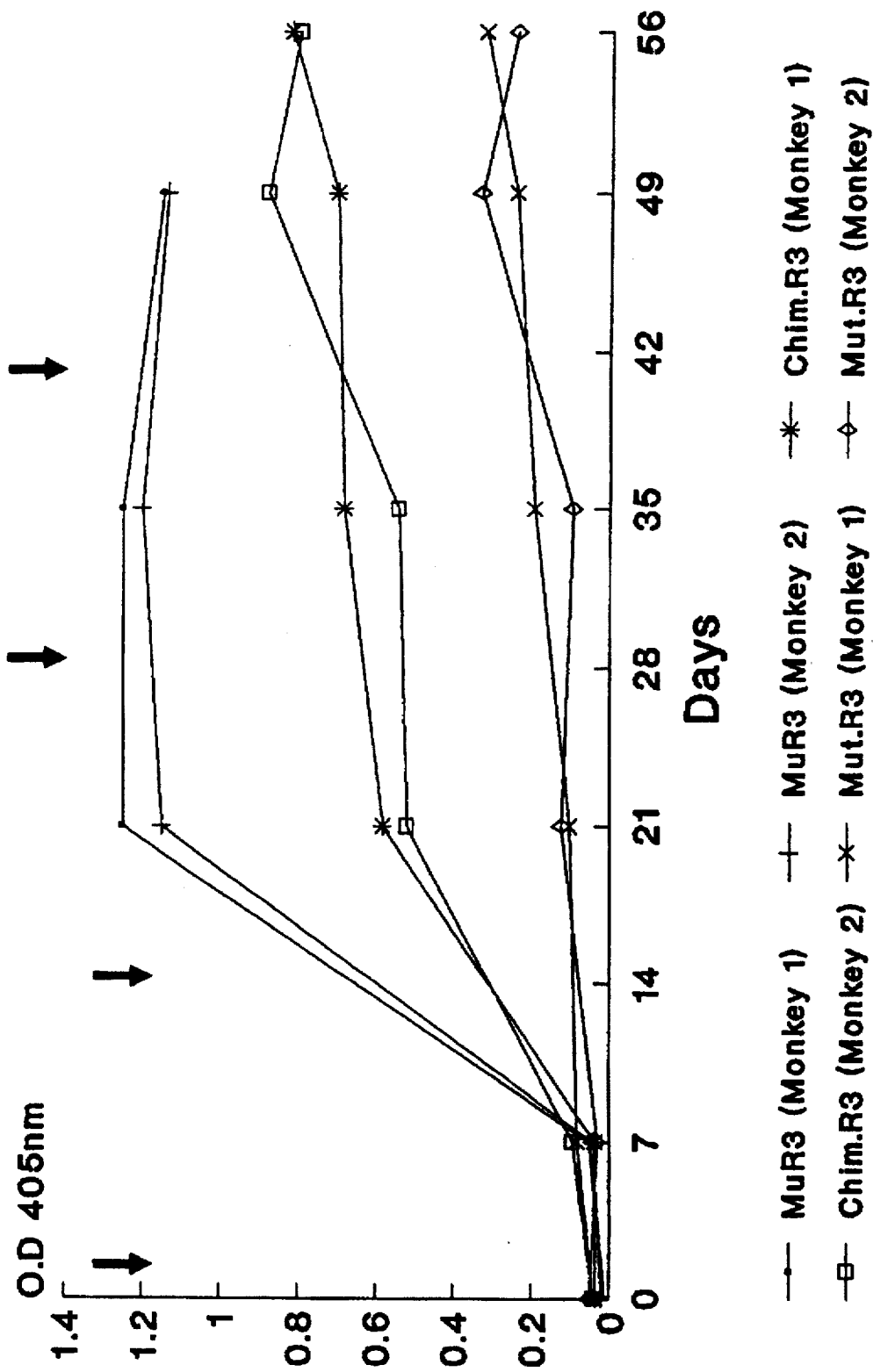

A high IgG response to murine R3 antibody was obtained when this antibody was used as immunogen. A lower but still measurable IgG response (1/10,000) to the murine R3 antibody was obtained when monkeys were immunized with the chimaeric antibody, contrary to the results obtained with the mutant Vh version (FIG. 6). With the mutant VH R3 antibody no response was measurable after two immunizations, and a small response (1/10,000) was measured after 4 immunizations.

EXAMPLE 10

Modification of the Variable Domain Sequences of IOR-T1 Murine Monoclonal Antibody to Humanize the Predicted T-cell Antigenic Sequences The variable region sequences of heavy and light chains of IOR-T1 were analyzed for T-cell antigenic sequences.

In the variable domain of the heavy chain 3 segments were predicted, they are:

1. FR1 between amino acids 2–21.
2. FR1, CDR1, FR2 between amino acids 29–43.
3. FR4, CDR3 between amino acids 97–111.

FIG. 7 shows a comparison with the most homologous human sequence and the replacement proposed, which are 5 at the FR1, 2 at the FR2 and 2 at the FR4.

The same procedure with the light chain (FIG. 8) rendered the following T-cell antigenic segments:

1. FR3 between amino acids 60–65.
2. FR3, CDR3 between amino acids 79–90.
3. CDR3 between aminoacids 93–95A.

After the analysis we proposed 5 replacement in FR3 at positions: 60, 63, 83, 85 and 87.

EXAMPLE 11

Modification of the Variable Domain Sequences of IOR-CEA1 Murine Monoclonal Antibody to Humanize the Predicted T-cell Antigenic Sequences The variable region sequences of heavy and light chains of IOR-CEA1 were analyzed for T-cell antigenic sequences.

In the variable domain of the heavy chain two segments were predicted, they are:

1. FR1 between amino acids 1–16.
2. CDR3 and FR4 between residues 96–110.

FIG. 9 shows a comparison with the most homologous human sequence and the replacements proposed, which are 7 at the FR1 and 2 at the FR4.

The same analysis with the light chain (FIG. 10) rendered the following T-cell antigenic segments:

1. FR1 between amino acids 1–14.
2. CDR2-FR3 between amino acids 55–70.
3. FR3-CDR3-FR4 between residues 74–100.

After the analysis we proposed 4 replacements in FR1 at positions 9, 10, 11 and 13, 11 replacements in FR3 at positions 58, 60, 63, 70, 75, 76, 78, 81, 83, 85 and 87, and 1 replacement in FR4 at position 100.

EXAMPLE 12

Analysis of Amphipatic Segments in Variable Regions of Immunoglobulin Families The program AMPHI was included as a subroutine in a program written for reading and processing the immunoglobulin sequences from the Kabat Data Base. In processing the sequences the following rearrangements were made:

Undefined amino acids of type GLX (possible GLN or GLU) were defined as GLN (both GLN and GLU have similar hydrophilicity indexes: −0.22 and −0.64 respectively).

Undefined amino acids of type ASX (possible ASN or ASP, with hydrophilicity indexes of −0.60 and −0.77) were defined as ASN.

Other undefined amino acids (empty spaces or "strange" symbols in the sequences were defined as XXX (unknown). The program AMPHI assigns a hydrophilicity value of 0.0 to these amino acids.

Sequences with more than 5 unknown amino acids (XXX) were not included in the analysis.

After this preliminary analysis each sequence was processed by the program AMPHI and the results are presented in the form of tables for each immunoglobulin family.

In tables I to VI the analysis for the six mouse heavy chain families is shown. "Predominant amphipatic regions" (PAR) could be defined at those present in more than 90% of the variable region sequences belonging to each family. For example, comparing the framework one (FR1), a PAR could be defined between the 11 and the 16 amino acid residues for the families I and II, by contrary families III and IV have not amphipatic regions in general from the first amino acid to the 30th. In families V and VI, smaller PARs could be defined from 12–14 and 12–15 residues respectively.

Humanization of the PARs would reduce immunogenicity in patients. The clustering of amphipatic regions in the immunoglobulin variable region frameworks supports the universality of the proposed method, i.e. to humanize these predicted T-cell epitopes by few point mutations.

---

We claim:

1. A method of modifying an antibody comprising:

comparing the framework amino acids of a variable domain of a first mammalian species with a group of framework amino acid residue variable domains of a second mammalian species;

determining a subgroup of the second mammalian species to which the first mammalian species most closely corresponds;

selecting the antibody from said subgroup whose framework is most similar to the first mammalian species' framework sequence;

identifying amino acid residues of the first mammalian species which differ from the amino acid residues of the selected second mammalian species framework and which are within T-cell antigenic sequences, with said amino acid residues being with T-cell antigenic sequences in the variable region of the immunoglobulins;

identifying only those amino acid residues which are not within a complementarity region or are not directly involved with canonical structures or Vernier zone; and replacing the amino acid residues in the first mammalian species framework which differ from the amino acid residues of the second mammalian species with the corresponding amino acid residues from the most similar second mammalian species thus identified; and obtaining the modified antibody.

2. The method of claim 1 wherein the first mammalian species is mouse.

3. The method of claim 1 wherein the second mammalian species is human.

4. The method of claim 1, wherein one or more heavy chain constant domains, the light chain constant domain, or both heavy and light chain constant domains of said first mammalian species antibody are replaced by the corresponding constant domain of the second mammalian species antibody.

* * * * *